(12) United States Patent
Dyer et al.

(10) Patent No.: US 7,758,469 B2
(45) Date of Patent: Jul. 20, 2010

(54) EXERCISE DEVICE VISUAL REPRESENTATION

(75) Inventors: David E. Dyer, Renton, WA (US); Sean Horita, Seattle, WA (US); James S. Birrell, Seattle, WA (US); Rodney P. West, Kirkland, WA (US); Jonathan M. Stewart, Seattle, WA (US)

(73) Assignee: Precor Incorporated, Woodinville, WA (US)

( * ) Notice: Subject to any disclaimer, the term of this patent is extended or adjusted under 35 U.S.C. 154(b) by 35 days.

(21) Appl. No.: 12/154,916

(22) Filed: May 28, 2008

(65) Prior Publication Data

US 2009/0298649 A1    Dec. 3, 2009

(51) Int. Cl.
*A63B 24/00*    (2006.01)

(52) U.S. Cl. ............... 482/4; 482/1; 482/8; 482/51; 482/70

(58) Field of Classification Search ............ 482/1, 482/4, 8, 9, 70, 71, 52; 5/600, 613, 652; 700/160, 169
See application file for complete search history.

(56) References Cited

U.S. PATENT DOCUMENTS

| | | | | |
|---|---|---|---|---|
| 4,512,567 A | 4/1985 | Phillips | ............... | 272/73 |
| 4,637,605 A | 1/1987 | Ritchie | ............... | 272/73 |
| 4,720,789 A | 1/1988 | Hector et al. | ............... | 364/410 |
| 4,955,602 A | 9/1990 | Rastelli | ............... | 272/76 |
| 4,976,435 A | 12/1990 | Shatford et al. | ............... | 273/148 |
| 5,149,084 A | 9/1992 | Dalebout et al. | ............... | 482/3 |
| 5,213,555 A | 5/1993 | Hood et al. | ............... | 482/57 |
| 5,364,271 A | 11/1994 | Aknin et al. | ............... | 434/61 |
| 5,466,200 A | 11/1995 | Ulrich et al. | ............... | 482/4 |
| 5,554,033 A | 9/1996 | Bizzi et al. | ............... | 434/247 |
| 5,591,104 A | 1/1997 | Andrus et al. | ............... | 482/7 |
| 5,645,513 A | 7/1997 | Haydocy et al. | ............... | 482/57 |
| 5,779,596 A | 7/1998 | Weber | ............... | 482/4 |
| 5,888,172 A | 3/1999 | Andrus et al. | ............... | 482/7 |
| 5,890,995 A | 4/1999 | Bobick et al. | ............... | 482/4 |
| 6,042,519 A | 3/2000 | Shea | ............... | 482/57 |
| 6,152,856 A | 11/2000 | Studor et al. | ............... | 482/8 |
| 6,227,968 B1 | 5/2001 | Suzuki et al. | ............... | 463/7 |
| 6,336,891 B1 | 1/2002 | Fedrigon et al. | ............... | 482/8 |
| 6,447,424 B1 | 9/2002 | Ashby et al. | ............... | 482/8 |
| 6,926,646 B1 * | 8/2005 | Nguyen | ............... | 482/71 |
| 2001/0001303 A1 * | 5/2001 | Ohsuga et al. | ............... | 482/5 |
| 2002/0019258 A1 | 2/2002 | Kim et al. | ............... | 463/36 |
| 2002/0055383 A1 | 5/2002 | Onda et al. | ............... | 463/36 |
| 2004/0005924 A1 * | 1/2004 | Watabe et al. | ............... | 463/36 |
| 2004/0043367 A1 | 3/2004 | Chou | ............... | 434/250 |
| 2007/0254778 A1 * | 11/2007 | Ashby | ............... | 482/5 |
| 2008/0161161 A1 * | 7/2008 | Pipinich et al. | ............... | 482/8 |
| 2008/0214357 A1 * | 9/2008 | Farinelli et al. | ............... | 482/8 |

* cited by examiner

*Primary Examiner*—Loan Thanh
*Assistant Examiner*—Shila Abyaneh
(74) *Attorney, Agent, or Firm*—Terence P. O'Brien; Todd A. Rathe

(57) ABSTRACT

An exercise device includes a member that moves through a selected one of a plurality of differently available paths. A display provides a visual representation of the movement of the first member.

29 Claims, 14 Drawing Sheets

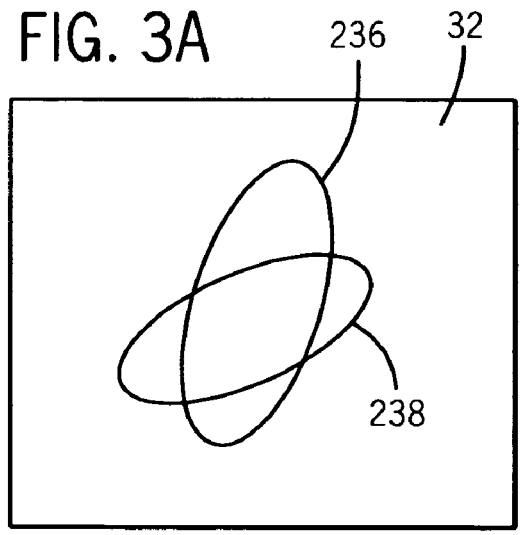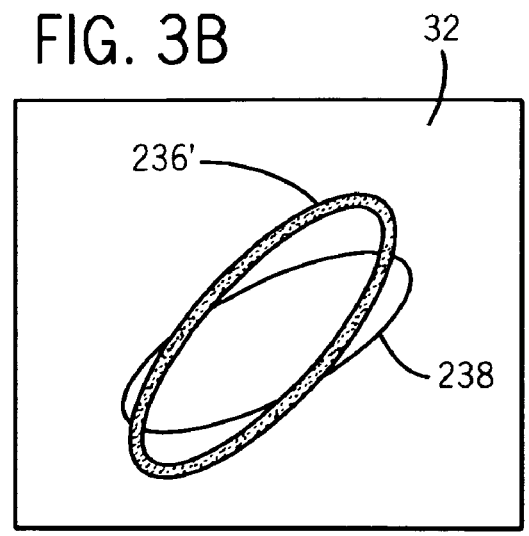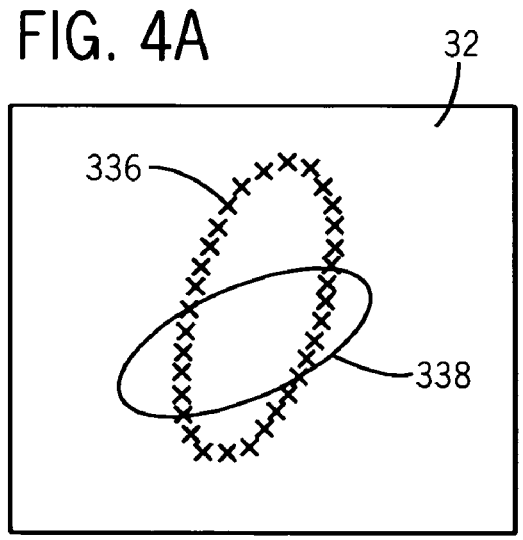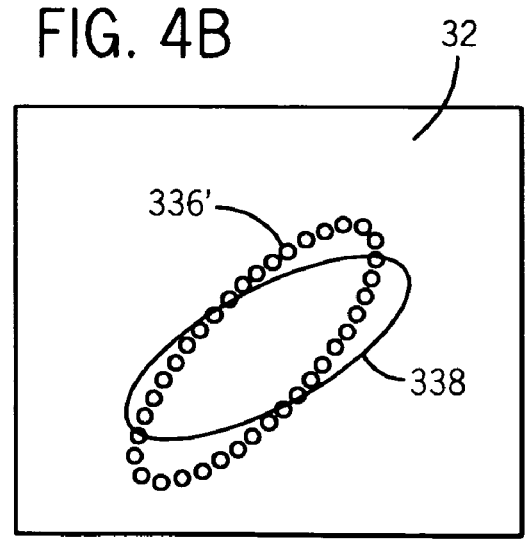

EXERCISE DEVICE VISUAL REPRESENTATION

CROSS-REFERENCE TO RELATED PATENT APPLICATIONS

The present application is related to co-pending U.S. patent application Ser. No. 11/646,882 filed on Dec. 28, 2006 by Jonathan M. Stewart, Rodney P. West, David E. Dyer, James S. Birrell and Sean Horita and entitled END OF TRAVEL STOP FOR AN EXERCISE DEVICE, the full disclosure of which is hereby incorporated by reference.

The present application is related to co-pending U.S. patent application Ser. No. 11/646,850 filed on Dec. 28, 2006 by Victor Pipinich, Robert Silbemagel and Sean Horita and entitled METRIC DISPLAY FOR EXERCISE EQUIPMENT, the full disclosure of which is hereby incorporated by reference.

BACKGROUND

Exercise devices having a limited and controlled path of motion may become monotonous to use over time. Some exercise devices may provide a greater degree of freedom of motion; however, with such exercise devices, it may be difficult to evaluate and monitor form and progress.

BRIEF DESCRIPTION OF THE DRAWINGS

FIGS. 3A and 3B are front elevational views of a portion of the display of the exercise device of FIG. 1 providing second visual representations of actual paths and a target path at different moments according to an example embodiment.

FIGS. 4A and 4B are front elevational views of a portion of the display of the exercise device of FIG. 1 providing third visual representations of actual paths and a target path at different moments according to an example embodiment.

DETAILED DESCRIPTION OF THE EXAMPLE EMBODIMENTS

Figure 1:
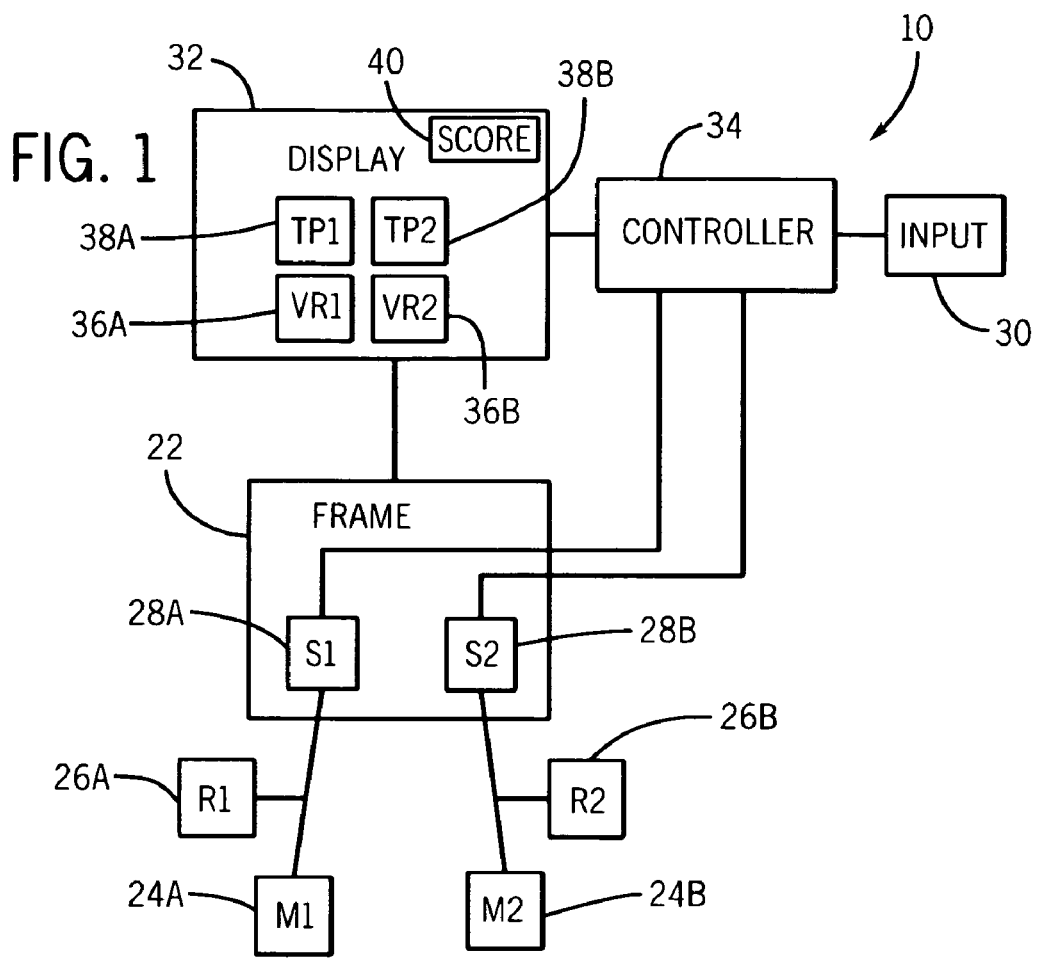
FIG. 1 is a schematic illustration of an exercise device according to an example embodiment.

FIG. 1 schematically illustrates an exercise device 10 according to an example embodiment. Exercise device 10 provides a person exercising (the user) with a multitude of different available paths and a greater degree of freedom of motion. As will be described in more detail hereafter, exercise device 10 further provides feedback in the form of a visual representation of the particular path taken by the user. In some embodiments, the feedback additionally provides user an indication of how closely the taken path corresponds to a goal or target path. As a result, exercise device 10 enables the user to better evaluate and monitor his or her form and progress towards health objectives.

As shown by FIG. 1, exercise device 10 includes frame 22, members 24A, 24B (collectively referred to as members 24), resistance supplies 26A, 26B (collectively referred to as supplies 26), sensors 28A, 28B (collectively referred to as sensors 28), input 30, display and 32 and controller 34. Frame 22 comprises one or more structures which serve as a base or foundation for remaining components of exercise device 10. Frame 22 movably supports members 24 such that each of members 24 may move in a multitude of different paths or ranges of motion. Towards this end frame 22 may include one or more joints, bearings, elastic members or other structures that facilitate movement of each of members 24 through or along a plurality of different paths or to different extents.

In one embodiment, frame 22 movably supports each of members 24 through a continuous and endless path such as a circle, oval (ellipse), or polygonal path. In another embodiment, frame 22 may movably support members 24 along multiple paths having distinct endpoints, wherein the endpoints are at different locations in space. For example, in one embodiment, members 24 may be supported so as to reciprocate or move back and forth along a linear segment, along an arcuate segment or along a complex segment having multiple twists and turns, wherein each segment has two distinct endpoints.

In one embodiment, frame 22 may movably support members 24 for movement along a substantially infinite number of paths which may differ from one another in two or more axes. For example, frame 22 may permit a user to take any of a continuum of paths for one or both of members 24 across a range of space. In another embodiment, frame 22 may movably support each of members 24 along paths which are predefined and which differ from one another by predetermined degrees.

Members 24 comprise structures extending from or supported by frame 22 that are configured to receive force applied by the user to effectuate exercise. Members 24 are further configured to use the force applied during exercise to move relative to frame 22 to almost instaneously change between different available paths with respect to frame 22 in response to force applied by a person to one or more of members 24. For example, in one embodiment, members 24 may be configured to exercise a person's lower extremities such as his or her legs. During such exercise, the person exerts a force with his or her legs against members 24 which results in members 24 moving through a selected path. By simply changing the amount of force or the direction of force applied to members 24 by his or her legs, a person may change the actual path taken by members 24 relative to frame 22. For example, a person may move his or her legs in a more forward or reverse direction to increase or decrease a stride length. A person may move his or her legs in a more or less vertical direction or apply force in a more or less vertical direction (change the vector in which forces applied to the member) to change a vertical height of the path of members 24. Such changes may occur solely in response to the force applied by persons legs to members 24 during exercise. In other words, person does not need to actuate a separate control to change the paths along with members 24 moved along which the person's legs move. The user-defined path or user-defined motion may be controlled solely in response to force applied by the same portion of a person that is exercising during exercise. In a similar fashion, members 24 may also or alternatively be configured to change between different paths in response to forces or the direction of forces applied to members 24 by other portions of a person's anatomy being exercised and which move with members 24 through one of a plurality of available paths during exercise.

In one embodiment, members 24 may comprise foot links, footpaths, pedals and/or steps configured to be engaged or pressed upon by a user's feet. In such an embodiment, members 24 may be elevated above a supporting floor or ground by frame 22. In such an embodiment, because members 24 receive force applied by a user's feet, members 24 are adapted to facilitate exercise of a user's legs or lower extremities. The path along which members 24 travel varies in response to force or the direction of force applied to members 24 by the user's legs and feet.

In one embodiment, members 24 may comprise bars, grips, arm links or other structures configured to be pressed upon by a person's hands or arms. For example, members 24 may be configured to be grasped by user's hands such that members 24 are moved upon application of force by the user's arms. Members 24 may alternatively be configured to be pressed upon by user's forearms, facilitating exercise of a user's arms. The path along which members 24 travel varies in response to force or the direction of force applied to members 24 by the user's arms, such as his or her forearms.

In one embodiment, members 24 comprise relatively rigid structures rigidly extending from frame 22 which movably support members 24. In other embodiments, members 24 may include flexible or elastomeric portions extending from frame 22. In some embodiments, members 24 may themselves include one or more articulating or pivoting joints.

Resistance supplies 26 comprise mechanisms configured to supply or apply resistance to movement of members 24 along the taken path. In the embodiment illustrated resistance supplies 26 supply a user selectable or user controllable degree or amount of resistance against movement along the taken path. In one embodiment, each of resistance supplies 26 may apply a varying amount of resistance through the different degrees or levels of friction such as with one or more friction brakes. In another embodiment, each of resistance supplies 26 may apply a varying amount of resistance through the use of different members having different elasticities. In yet another embodiment, each of resistance supplies 26 may create resistance through the use of one or more electrical or magnetic fields. For example, resistance supplies 26 may comprise generators having magnets, wherein movement through a magnetic field is resisted and wherein such resistance is adjustable. In another embodiment, resistance supplies 26 may include fan blades and the like which are adjustable to provide different degrees of resistance as the blades move through air. In still other embodiments, resistance supplies 26 may have other configurations.

Sensors 28, input 30, display 32 and controller 34 each serve as part of a feedback system regarding the path taken by members 24. Sensors 28 comprise mechanisms configured to detect or sense the path selected by the user and taken by members 24 in response to the application of force to members 24 by the user. In one embodiment, sensors 28 may comprise one or more optical detectors such as one or more optical emitters and detectors. In another embodiment, sensors 28 may comprise individual cameras configured to detect movement of members 24 in space. In other embodiments, sensors 28 make comprise other mechanisms configured to detect and track movement of members 24, such as, for example, one or more accelerometers.

Input 30 comprises one or mechanisms configured to permit the entry of selections, commands and/or data into exercise device 10. In one embodiment, input 30 may be configured to facilitate entry of such selections, commands or data by the user of exercise device 10. For example, in one embodiment, input 30 may comprise a touchpad, a touch screen, a keyboard, a mouse, one or more dials, one or more pushbuttons: one or more rocker switches or a microphone and appropriate voice recognition software. In other embodiments, input 30 may also, or alternatively, include an electronic plug-in or port configured to receive selections, commands and/or data from an external electronic device. In yet another embodiment, the input 30 may comprise an input device configured to receive selections, commands and/or data, wherein such input is transmitted to exercise device 10 across the Internet or an intranet in a wired or wireless fashion.

Display 32 comprises a monitor, screen or other device configured to present visual information to a user of exercise device 10 while the user is exercising. For example, display 22 may comprise an LCD screen. In another embodiment, display 32 may comprise an array or series of individual lights or light emitting diodes that are selectively illuminated to provide visual information. In one embodiment, display 32 may be a part of a touch screen which also serves as input 30.

In one embodiment, display 32 is fixedly mounted to frame 22 and supported such that a person may view display 32 when exercising. In yet another embodiment, display 32 may be provided by a portable device which is removably connectable to exercise device 10. For example, display 32 may be provided by a hand held personal data device such as a personal digital assistance (PDA), portable media player (such as an IPOD), MP3 player or similar portable device having a display which is connected to controller 34 via a plug-in or port or wirelessly, wherein the portable device is supported by frame 22 during such exercise or is held by the user exercising.

Controller 34 comprises one or more processing units configured to receive signals from sensors 28, to receive selections, commands or data from input 30 and to generate control signals directing the operation of at least display 32 and potentially additionally directing the operation of frame 22 and resistance supplies 26. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 34 may be embodied as part of one or more application-specific integrated circuits (ASICs). Unless otherwise specifically noted, the controller is not limited to any specific combination of hardware circuitry and software, nor to any particular source for the instructions executed by the processing unit.

In the embodiment illustrated, controller 34 generates control signals based upon signals received from sensors 28 that cause display 32 to present a visual representation of the path taken by at least one of members 24. For example, in one embodiment, controller 34 may generate control signals causing display 32 to present an animation (or other representation) of a person interacting with one or both of members 24 to move one or both of members 24 through the actual path being taken by members 24. In another embodiment, controller 34 may generate control signals causing display 32 to present an animation of an entirety or a portion of one or both of members 24 moving through their actual taken paths. In yet another embodiment, controller 34 may generate control signals causing display 32 to present an animation of a point or other icon moving in the actual taken path. It still other embodiments, controller 34 may generate control signals causing display 32 to present an outline of a portion or the entirety of the current path being taken by one or both of members 24. In still other embodiments, other visual representations communicating the path currently being taken by one or both of members 24 may be presented.

In the example illustrated, controller 34 generates control signals causing display 32 to present visual representations of actual paths 36A and 36B (collectively referred to as actual paths 36) which visually represent the path selected by the user and taken by members 24A and 24B, respectively. In one embodiment, two distinct actual paths are presented. In such an embodiment, both actual paths 36 may be concurrently presented by display 32 or may alternatively be sequentially presented in a timed fashion or based upon commands received via input 30 from the user. In another embodiment where the paths taken by members 24 mirror one another or which are substantially the same as one another except for potentially being out of phase with one another, controller 34 may present a single visual representation of the actual path selected by the user and taken by members 24.

As further shown by FIG. 1, in the example illustrated, controller 34 is also configured to generate control signals causing display 32 to present at least one visual representation of an objective, goal or target path. The target path may be chosen based upon input from a user via input 30 or based upon an exercise routine, exercise program or exercise objectives selected by a user, a trainer or some other source and entered via input 30 or contained in the memory of an exercise computer program or the like.

As with the visual representation(s) of the actual path taken by members 24, the target path(s) may comprise an animation of a person interacting with one or both of members 24 to move one or both of members 24 through the target path desired to be taken by members 24. In another embodiment, controller 34 may generate control signals causing display 32 to present an animation of an entirety or a portion of one or both of members 24 moving through target paths. In yet another embodiment, controller 34 may generate control signals causing display 32 to present an animation of a point or other icon moving in the target path. It still other embodiments, controller 34 may generate control signals causing display 32 to present an outline of a portion of or the entirety of the target path to be taken by one or both of members 24. In still other embodiments, other visual representations communicating the target path to be taken by one or both of members 24 may be presented.

As shown by FIG. 1, in the example illustrated, controller 34 is configured to generate control signals directing or causing display 32 to present target paths 38A, 38B representing the target paths for members 24A and 24B, respectively. In such an embodiment, both target paths 38 may be concurrently presented by display 32 or may alternatively be sequentially presented in a time fashion or based upon commands received via input 30 from the user. In another embodiment where the paths taken by members 24 mirror one another or which are substantially the same as one another except for potentially being out of phase with one another, controller 34 may present a single visual representation of the target path.

In one embodiment, controller 34 generates control signal such that the one or more visual representations of the actual path(s) 36 and the one or more visual representations of the target path(s) 38 are concurrently presented by display 32 to a user. As a result, the user may be better able to visually compare the actual path being taken as represented by the one or more actual paths 36 and the one or more target paths 38. By allowing a user to better visually compare the taken and target paths, exercise device 10 enables a user to better evaluate his or her form as well as his or her progress towards an exercise objective.

In one embodiment, the one or more visual representations of actual paths 36 taken and the one or more target paths 38 are overlaid with respect to one another to you and further enhance the ability of the user to compare such paths. In yet other embodiments, the actual paths 36 and the target paths 38 may alternatively be positioned side-by-side or in a top in a relationship. In yet another embodiment, the one or more actual paths 36 and the one or more target paths 38 may be presented at distinct times by display 32.

As schematically shown by FIG. 1, controller 34 also generates control signals which caused an indication or score 40 indicating a degree of correlation or matching between the actual path being taken by members 24 and the target path for members 24 to be communicated in real time to the user while the user is actually exercising and moving members 24 through the taken paths. In one embodiment, the indication may be presented visually upon display 32. In another embodiment, controller 34 may provide the indication in an audible fashion such as with one or more beeps, audible words or phrases. In the example illustrated, controller 34 is selectively operable in one or more of a plurality of different modes in which the score 40 is presented in different manners. In one mode, score 40 may be presented in multiple manners at the same time. For example, score 40 may be visually represented in multiple different manners at one time. Score 40 may represented by both audible and visual indications.

Although FIG. 1 illustrates exercise device 10 as having to members 24, 2 resistance supplies 26 and two sets of sensors 28, facilitating interaction with two legs or two arms of a person exercising, in other embodiments, exercise device 10 may alternatively include a single member 24, is in the resistance supply 26 and a single group of sensors 28. For example, exercise device 10 may have a single member 24 which is engaged by only one or one leg. Exercise device 10 alternatively be configured such that a single member 24 is engaged by both arms are both legs. For example, exercise device 10 may simulate ski boarding where both legs engaging single member. Although exercise device 10 is illustrated as having dedicated groups of resistance supply 26 in groups of sensors 28 dedicated to each member 24, in other embodiments, more than one of members 24 may share the same resistance supply 26 or the same group of sensors 28.

Figure 2:
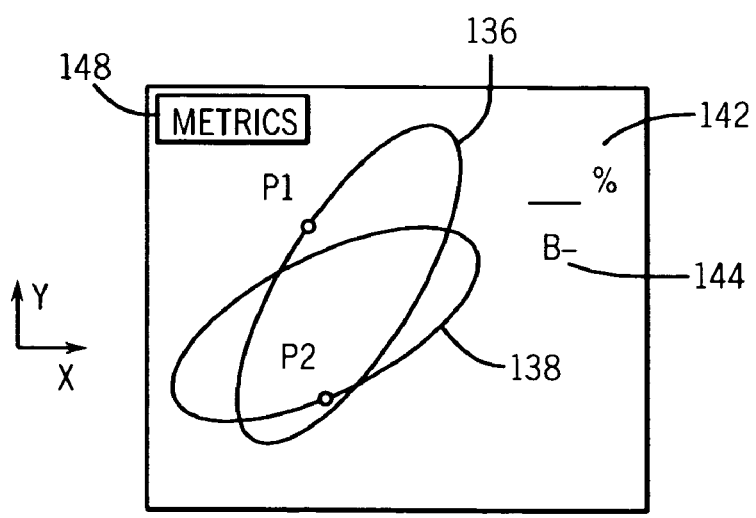
FIG. 2 is a front elevational of view of a portion of a display of the exercise device of FIG. 1 providing first visual representations of an actual path and a target path according to an example embodiment.

FIGS. 2-8 schematically illustrate various example modes by which the actual path, the target path and the score 40 may be visually presented by controller 34 and display 32. In the example illustrated, members 24 move through or along paths which are substantially identical to one another at any moment in time, but which are substantially 180 degrees out of phase with one another such as when a person's legs or arms move in opposite directions at any moment in time during running or walking. As shown by FIG. 2, controller 34 generates control signals causing display 32 to present a visual representation of the actual path 136 being taken a members 24 and also causing display 32 to concurrently present a visual representation of a target path 138. The actual path 136 being taken and the target path 138 are a subset of the total number of available paths available for members 24 as provided by frame 22. In the example illustrated, each of the different paths available to members 24 comprises a continuous or endless loop, wherein for each X axis coordinate in space, each different path has a distinct Y axis coordinate in space. In the example illustrated, both of the available paths depicted, path 136 and path 138, have points P1 and P2, respectively, having the same X axis coordinate but having different Y axis coordinates. Alternatively, for each Y axis coordinate in space, each different path has a different X axis coordinate in space. Alternatively, for each Z axis coordinate in space, each different path has a different X axis coordinate in space or a different Y axis coordinate in space.

As shown in FIG. 2, controller 34 generates control signals causing display 32 to present a visible numerical score 142, such as a percent score, a number on a scale, and the like. In the example illustrated, controller 34 also causes display 32 to present a letter grade 144 such as "S" for satisfactory, and "A–" for a high degree of correlation or a "D" for a relatively low degree of correlation or matching. In other embodiments, controller 34 may generate control signals causing display 32 to present one of either a numerical score or a letter grade.

As schematically shown by FIG. 2, controller 34 may also generate control signals causing display 32 to present one or more metrics 148 along with the scores 142, 144 or with the visual representations of the paths 136, 138. Examples of metrics include, but are not limited to, heart rate, calories burned, a lapsed exercise time and the like. Such metrics 148 may be visually displayed by display 32 in each and every embodiment described hereafter.

FIGS. 3A and 3B illustrate controller 34 operating in a second mode in which controller 34 presents the score 40 in a second manner. In particular, controller 34 is configured to cause display 32 to vary a visual characteristic of the actual path being presented based upon the extent to which the actual path matches are corresponds to the target path. In the example shown in FIGS. 3A and 3B, controller 34 varies a thickness and a color or brightness of the line representing actual path 236 based or depending upon the extent to which the actual path matches are corresponds to the target path. FIG. 3A illustrates the actual path 236 overlaid with respect to a target path 238 at a first moment in time. FIG. 3B illustrate the actual path 236' being taken at a second moment in time and overlaid with respect to the target path 238. As the actual path 236 approaches the target path 238, controller 34 increases a thickness of the line representing the actual path 236. In the example illustrated, controller 34 also causes the brightness or the color of the graphic representing actual path 236 to change. For example, in one embodiment, the color of actual path 236 may become brighter as it approaches target path 238. In another embodiment, the color of actual path 236 may change, such as from a red color to a green color, as the actual path 236 more closely corresponds to the target path 238. Such changing of one or both of the thickness of the line representing actual path 236 or the color or brightness of a line representing actual path 236 may gradually change in a continuous fashion or may change in a stepwise fashion as particular matching thresholds are met.

Although FIG. 3B illustrates the line representing actual path 236 as increasing a thickness as it more closely corresponds to the target path 238, this relationship may be reversed. In particular, the line may alternatively become thinner as the actual path 236 approaches target path 338. In other embodiments, the degree or indication of correlation between the target path 236 and actual path 238 may alternatively be represented by changing a characteristic of the graphic visually representing the target path 238. For example, the thickness, color or brightness of the line representing target path 238 may change based upon the degree of correlation between the two paths. In one embodiment, the user may select, using input 30, the manner in which one or both of the visual representations of actual path 236 and target path 238 are changed in response to changes in the actual path being taken and sensed by sensors 28 (shown in FIG. 1).

FIGS. 4A and 4B illustrate controller 34 operating in a third mode in which controller 34 presents the score 40 in a third manner. In particular, controller 34 is configured to cause display 32 to vary a visual characteristic of the actual path being presented based upon the extent to which the actual path matches or corresponds to the target path. In the example shown in FIGS. 4A and 4B, controller 34 varies the individual graphic points or icons representing actual path 336 based upon or depending upon the extent to which the actual path matches or corresponds to the target path. FIG. 4A illustrates the actual path 336 overlaid with respect to a target path 238 at a first moment in time. FIG. 4B illustrate the actual path 336' being taken at a second moment in time and overlaid with respect to the target path 338. As the actual path 336 approaches the target path 338, controller 34 changes the graphic characters representing the actual path 336 from a series of x's to a series of o's. In other embodiments, other graphic symbols, characters or points may be employed to represent different degrees of correlation. In particular embodiments, the degree of correlation may also be represented in the same manner discussed above with respect to FIGS. 3A and 3B. For example, the size of the graphic symbols, or color or their brightness may also change based on the degree of correlation between such paths. Such changing of the graphic characters representing actual path 236 or the graphic characters representing actual path 236 may gradually change in a continuous fashion or may change in a stepwise fashion as particular matching thresholds are met.

Figure 5A:
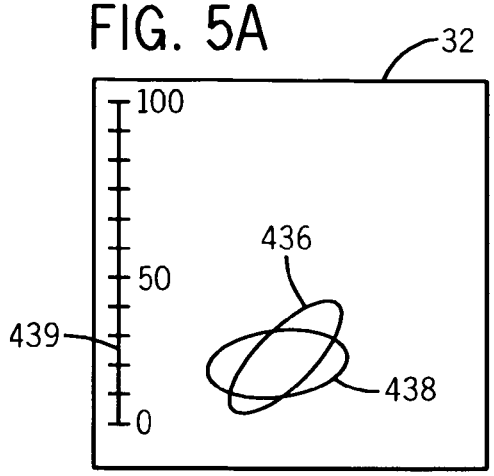
FIGS. 5A and 5B are front elevational views of a portion of the display of the exercise device of FIG. 1 providing fourth visual representations of actual paths and a target path at different moments according to an example embodiment.
Figure 5B:
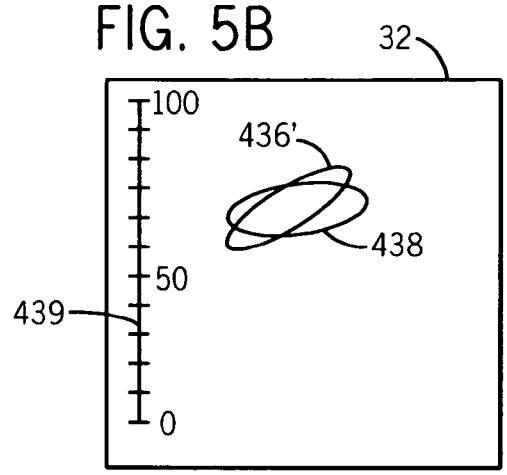

FIGS. 5A and 5B illustrate controller 34 operating in a fourth mode in which controller 34 presents the score 40 in a fourth manner. In particular, controller 34 is configured to cause display 32 to vary a location of the paths 436, 438 presented based upon the extent to which the actual path through 436 matches or corresponds to the target path 438. In the example shown in FIGS. 5A and 5B, controller 34 varies the vertical location at which paths 436 and 438 are presented based upon or depending upon the extent to which the actual path matches or corresponds to the target path. In the example illustrated, controller 34 further generate control signals causing display 32 to provide an index or scale 439, wherein the vertical location of paths 436 and 438 with respect to the scale 439 is based upon the degree of correlation or matching between the paths. 100531 FIG. 5A illustrates the actual path 436 overlaid with respect to a target path 438 at a first moment in time. FIG. 5B illustrates the actual path 436' being taken at a second moment in time and overlaid with respect to the target path 438. As the actual path 436 approaches the target path 438, controller 34 changes the vertical location of the visual representation representing the actual path 436. In particular, paths 436' and 438 are depicted at a higher vertical location as compared to that shown in FIG. 5A.

In other embodiments, the relative positioning of the visual representations of the paths may change in other manners. For example, instead of moving up as the degree of correlation increases, the visual representations may alternatively move down as the visual representations more closely match. Instead of moving vertically, the visual representations may move to the left, the right or diagonally depending upon the degree of correlation between the paths. In one embodiment, the positioning of the paths on the screen to communicate matching may be combined with other modes such as one or more of the modes shown in FIGS. 2-4. Such changing of the location of the visual representations of the paths on display 32 may gradually change in a continuous fashion or may change in a stepwise fashion as particular degree of matching thresholds are met.

In each of the modes shown in FIGS. 2-5, the actual path and the target path were visually represented by a line or other series of one or more graphic characters in the shape of the paths. FIG. 6 illustrates another mode that may be selected by user via input 30, wherein the actual path and the target path at any moment in time are represented by animations of one or both of members 24 and/or at least anatomical portions of a person moving along the paths. In the particular example illustrated in FIG. 6, controller 34 generates control signals causing display 32 to present a visible or visual representation of a person 510 in contact or engagement with visual representations 512 of members 24A, 24B. The animation illustrates movement of the person's legs and feet as well as the visual representations 512 along an actual path being taken at a particular moment in time. Concurrently with the presentation of the animation of the person 510 moving through the actual path, controller 34 also generates control signals causing display 32 to present an animation comprising a visual representation of a person 520 in contact or engagement with the same visual representations 512 representing members 24 (shown in FIG. 1) moving through or along the target path.

Because display 32 illustrates an actual representation of a person and/or illustrates a representation of the members 24 which are being moved during exercise, the person exercising may be able to better understand the differences between the present actual path being taken and the target path. As a result, the user, while exercising, may be better able to make adjustments such that his or her actual path more closely matches the target path.

Figure 6A:
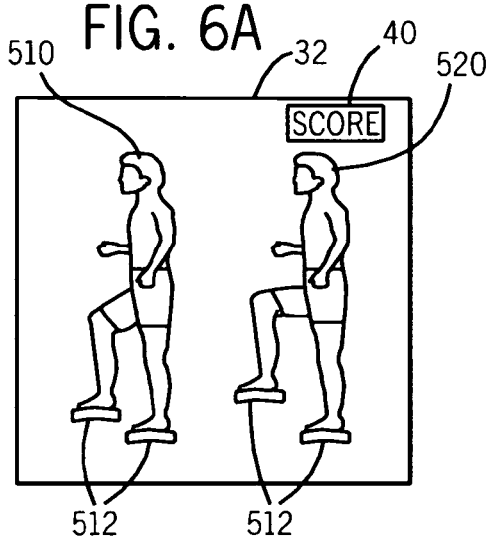
FIG. 6 is a front elevational of view of a portion of a display of the exercise device of FIG. 1 providing fifth visual representations of an actual path and a target path according to an example embodiment.
Figure 6B:
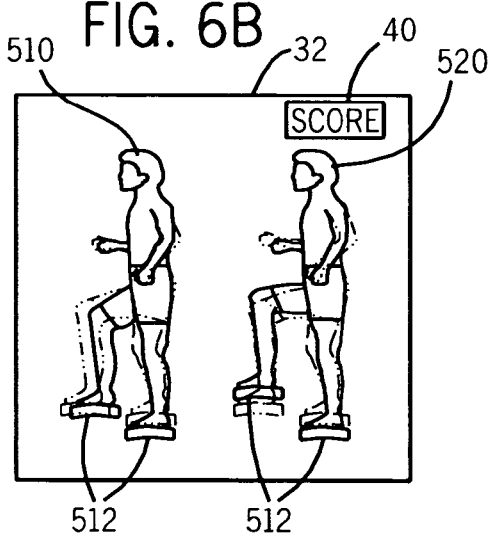

In the particular example illustrated in FIG. 6, persons 510 and 520 as well as visual representations 512 are presented in a side-by-side manner. As shown by FIG. 6B, in another mode selectable by a user via input 30, persons 510 and 520 as well as visual representations 512 may be overlaid with respect to one another to potentially better communicate to a user the differences between actual path and the target path. In such an embodiment, the overlaid graphics may have different colors or different brightnesses to distinguish between the two sets of graphics illustrating the actual path and the target path. Although FIG. 6 illustrates an embodiment where the user's legs and feet traverse the path, the graphic shown in FIGS. 6A and 6B may alternatively illustrate movement of other portions of the user, such as his or her arms, where his or her arms engage members 24 (shown in FIG. 1).

In addition to illustrating the actual path and the target path using persons 510, 520 and/or visual presentation 512, controller 34 the also cause display 32 to present the indication or score 40 according to any of the modes described above with respect to FIGS. 2-5. For example, a numerical or letter grade score may be provided as shown in FIG. 2. The characteristic of the lines or graphic marks forming persons 510, 520 or visual representations 512 may be changed depending on the degree of matching of the paths. For example, the color of the person 510, 520 or the color of visual representations 512 may be changed depending on the degree of matching. The location at which persons 510, 520 and visual representations 512 upon display 32 may also be varied in a manner similar to that shown and described with respect to FIGS. 5A and 5B to communicate a score or degree of matching. In one embodiment, one or more or even all of the aforementioned modes may be combined with the mode shown FIG. 6 to indicate to a person exercising the degree of matching of the paths.

Figure 7A:
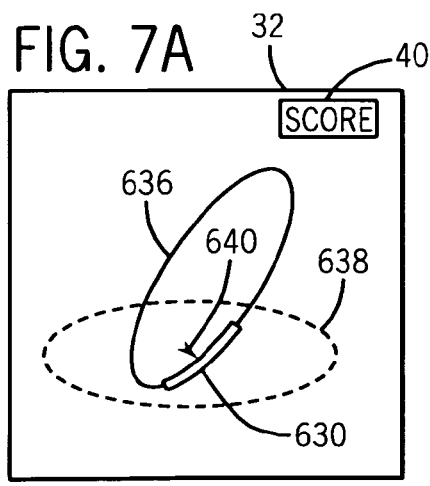
FIGS. 7A and 7B are front elevational views of a portion of the display of the exercise device of FIG. 1 providing sixth visual representations of actual paths and a target path at different moments according to an example embodiment.
Figure 7B:
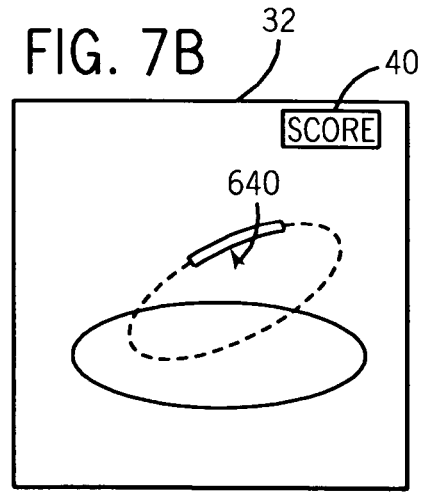

FIGS. 7A and 7B illustrate controller 34 generating control signals causing display 32 providing visual representations of the actual path and the target path in yet another mode which may be selected by a person via input 30. As shown by FIGS. 7A and 7B, controller 34 generates control signals such that display 32 presents only a portion 630 of the actual path 636 being taken. Portion 630 is overlaid with respect to the actual path 638. Portion 630 overlays or encompasses the precise point along the path at any particular moment in time. As shown in FIG. 7A and 7B, the remainder of the path 636 may be illustrated in another manner, such as with lighter line, with broken lines, or with lines or a series of spaced symbols of a color or form different from the lines or graphic symbols that form portion 630. In one embodiment, the remainder of path 636 may not be presented.

As shown by FIGS. 7A and 7B which illustrate display 32 at different moments in time, as a user moves along the current path, portion 630 also correspondingly moves on display 32. As a result, the user may better be able to specifically identify where he or she is along the path. This may also permit the user to better compare his or her precise position along the actual path being taken with respect to the target path 638 and to better able to make adjustments to more closely match the actual path 636 with the target path 638.

In some embodiments, controller 34 may be configured to generate control signals causing display 32 to present a pointer 640, or some other more precise graphic, precisely indicating where along portion 630 and path 636 that one or both the members 24 currently reside. In particular embodiments, portion 630 may be omitted in lieu of pointer 640.

As further shown by FIGS. 7A and 7B, controller 32 may also generate control signals causing the indication or score 40 to be presented by display 32. The indication or score 40 may have various forms such as one or more the forms described above with respect to FIGS. 2-5. For example, portion 630 or pointer 640 may change in size, shape, color, brightness or the like depending upon the degree of matching. The location of the portion 630, pointer 640 and path 638 along display 32 may change depending upon the degree of matching.

Figure 8A:
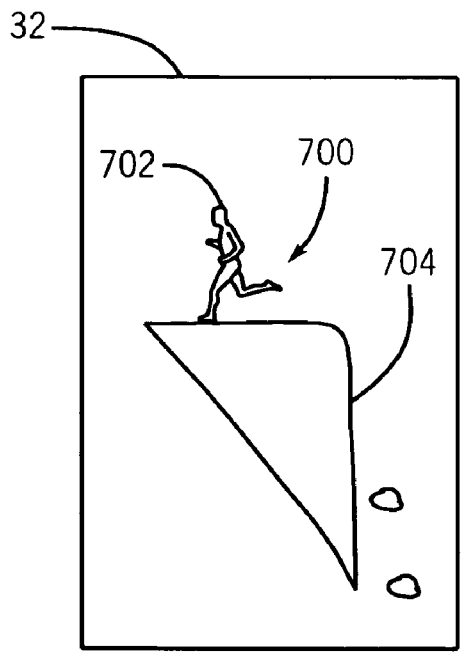
FIGS. 8A and 8B are front elevational views of a portion of the display of the exercise device of FIG. 1 providing a motivational graphic at different moments according to an example embodiment.
Figure 8B:
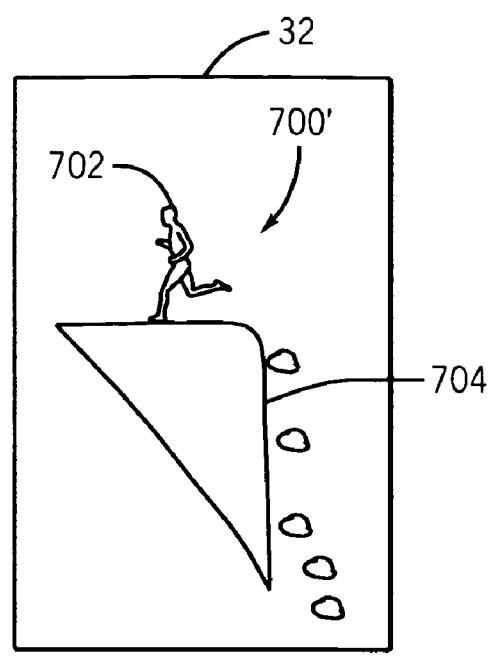

FIGS. 8A and 8B illustrate a portion of display 32, in response to control signals from controller 34 (shown in FIG. 1), presenting a motivational graphics 700 and 700', respectively, at different moments in time. The motivational graphic 700 varies depending upon the degree of correlation or matching between the actual path being taken by the user who is exercising and the target path. FIG. 8A is presented by display 32 when the actual path closely corresponds with the target path. FIG. 8B is presented when the actual path more greatly differs from the target path.

In the example illustrated, motivational graphic 700 comprises an animation. In particular, motivational graphic 700 comprises an animation of a person 702 running away from a collapsing, cascading cliff 704. In the example illustrated, as the actual path more closely matches the target path, controller 34 (shown in FIG. 1) generates control signals causing display 32 to present the animated person 702 farther away from cliff 704. As the actual path more greatly differs from the target path, person 702 moves closer to cliff 704. In this manner, the user who is exercising is presented with a graphical game-like motivation, staying away from cliff 704. In other embodiments, other motivational graphics, whether comprising stationary graphics or animated graphics, may be employed. Such graphics may be employed alongside, in a sequential manner to or in lieu of the display presentations shown in FIGS. 2-7.

Figure 9A:
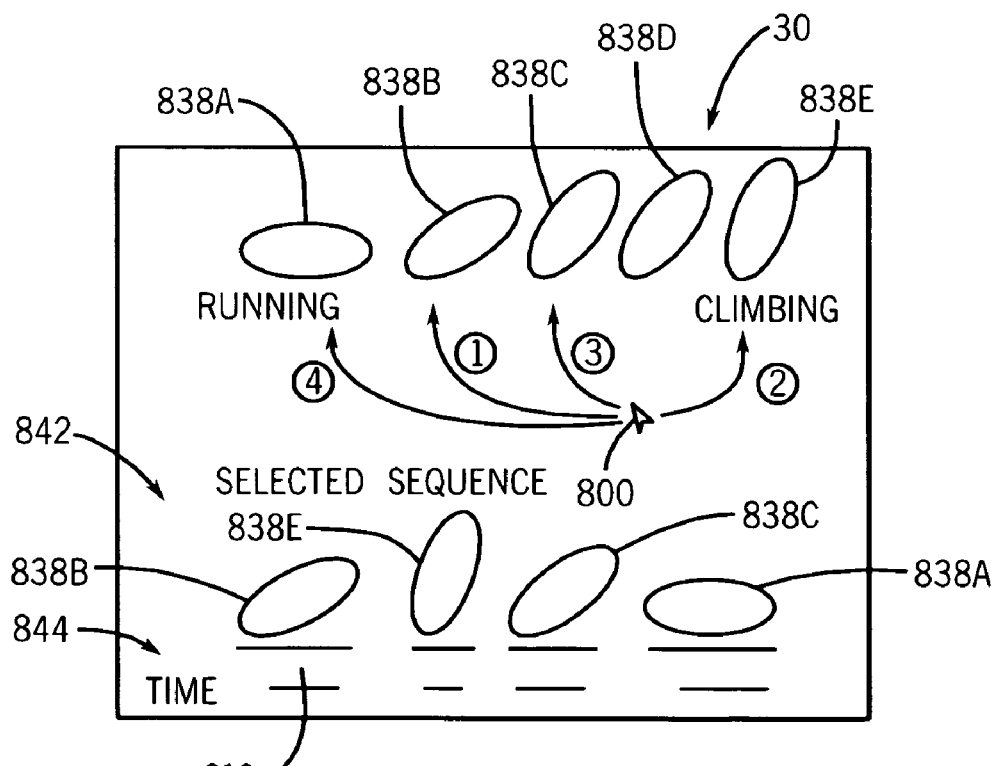
FIG. 9A is a front elevational view of a portion of a screen of an input of the exercise device of FIG. 1 schematically illustrating selection of a path sequence or routine according to an example embodiment.

FIG. 9A illustrates a portion of input 30 according to one embodiment. In the example illustrated, input 30 comprises a display screen which includes a mouse, touchpad, stylus or other device for manipulating a pointer icon 800 on the screen. As noted above, one embodiment, the screen employed as part of input 38 be incorporated as part of display 32.

FIG. 9A illustrates the display screen of input 30 operating in response to control signals from controller 34. FIG. 9A illustrates input 30 during selection of an exercise routine for exercise device 10 (shown in FIG. 1). In particular, the display screen of input 30 provides or presents a plurality of the different available target paths 838A, 838B, 838C, 838D and 838E (collectively referred to as target paths 838 provided by frame 22 and members 24 (shown in FIG. 1)). In the example illustrated, such paths range from a substantially horizontal oval or elliptical running path 838A (on the left) to a substantially vertical climbing path 838E (on the right). The display screen of input 30 further provides visual representations of the selected paths and their sequence in a selected sequence portion 842 of the screen as well as selected time periods for each of the selected individual paths in a selected time portion 844 of the screen.

As schematically represented by FIG. 9A, a user may select or create a desired exercise routine by manipulating the mouse, touchpad, stylus or other device to move pointer icon 800 in a sequential manner between the available target paths and clicking or otherwise selecting individual target paths in a desired order from the available paths. In the example illustrated, target path 838B is first selected, followed by target paths 838E, 838C and 838A. Target path 838E is not chosen. As each of the target paths 838 are selected, the chosen target paths are further automatically depicted in their selected order in the selected sequence portion 842 of the display screen. Alternatively, you chosen paths may be dragged and dropped to the sequence locations using the pointer icon 800.

In the embodiment illustrated, the user may further move the pointer icon 800 to the time location 812 beneath each path in the selected sequence portion of the screen and may enter, via numerical keypad or other device, a desired period of time that the particular path chosen is to be the target path during the particular exercise routine. In one embodiment, the created exercise routine including the order or sequence of the selected target paths and their associated times may be saved in a memory associated with controller 34 or in a portable memory such as in a memory associated with a portable media device of the user.

In the example illustrated, input 30 is illustrated as using a pointer icon 800. In other embodiments, other input device may be employed for selecting from the set of available target paths. In particular embodiments, the time periods for each of the selected target paths may alternatively be automatically set or may be predetermined. In one embodiment, in place of providing a visual representation of the actual target paths 838, each target paths may alternatively be identified in other fashions. For example, different target paths may be identified with different names and numbers or degrees of difficulty.

The time period for each chosen target path may comprise an absolute numerical values such as three minutes or may comprise a start time and a stop time. In one embodiment, the time value for each selected target path may count down or count up during exercise as the time period for the selected target path is consumed.

Overall, input 30 enables a user to preprogram a desired exercise routine by selecting individual target paths their order in their periods of use. Input 30 is further configured to enable exercise routines to be supplied from external sources. For example, in one embodiment, input 30 may include a port, plug-in, wireless adapter, receiver or other communication interface, a memory card reader/slot, disk drive or other device configured to facilitate input of previously created exercise routines. Such exercise routines may be downloaded from a network or Internet or maybe contained on portable disks, cards or the like. Such exercise routines may be supplied by the user's trainer, wherein the exercise routines may be customized for the particular user's exercise objectives.

In one embodiment, a trainer may go through an exercise routine on a similar or identical exercise device, wherein the trainer's exercise routine (the sequence of paths taken by the trainer on a similar exercise device) are sensed or otherwise captured by camera or one or more sense as associated with the trainer or the exercise device. The sensed or captured exercise routine is then analyzed and broken down into the one or more paths actually taken by the trainer. This analysis of the actual paths taken by the trainer and conversion to target paths for use by the trainees may be performed by controller 34 or by a controller or one or more processing units external to the exercise device of the user, such as an external computer or server. The actual paths taken by the trainer are then either stored for subsequent use as target paths by one or more users or are transmitted in real time (substantially instantaneously as the trainer is going through the desired routine for the trainees) via a network or intranet as target paths to multiple users or trainees. The created target paths are presented on each user's display 32.

The above method enables multiple users, potentially at remote locations, to follow the actions of a trainer, simulating an exercise class provided by the trainer. At the same time, in addition to observing the trainer on his or her monitor screen or in person, the person exercising may also observe a visual graphical representation of the actual movements or paths taken by the trainer on his or her display 32. On top of this, the user may observe a graphical representation of the actual path being taken by the user, permitting the user to better compare his path with the trainer's path. In some embodiments, the person who is exercising also receives a score or indication of how well he or she is mimicking or following the trainer during an exercise routine. The score would indicate the degree of correlation between the actual paths or motions taken by the user who is exercising to the actual paths or motions taken by the trainer which are used as the "target" paths.

Figure 9B:
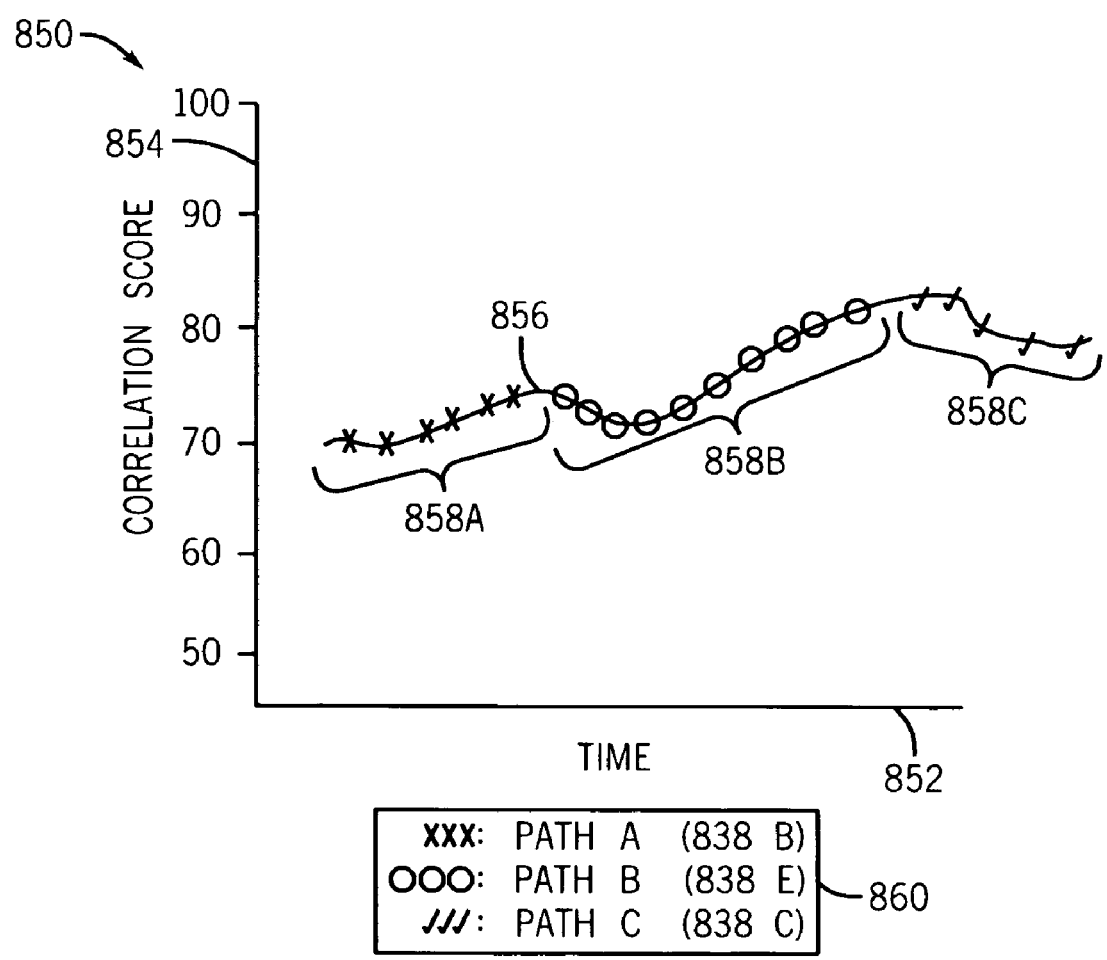
FIG. 9B is a front elevational view of a portion of a screen of an input of the exercise device of FIG. 1 schematically illustrating the display of a correlation score for target paths and selected paths over time according to an example embodiment.

FIG. 9B illustrates another mode of operation 850 available for exercise device 10 (shown in FIG. 1). In many of the previous modes, controller 34 generated control signals causing display 32 to present the person exercising with a graphic, score, grade or other visual representation indicating a degree of correlation or matching between the persons actual taken path and the selected target path at the particular moment in time. In mode 850, controller 34 generates control signals causing display 32 to provide the person exercising with a visual representation of his or her performance over time. In particular, controller 34 generates control signals causing display 32 provider visual representation indicating a degree to which the persons actual path(s) matched the selected target path(s) over time. As a result, the person exercising can better evaluate his or her overall workout performance.

In one embodiment, in addition to providing the matching or correlation score of a person over time during a workout (or during multiple workouts at different times or at different days—a historical perspective) mode 850 may also provide the person exercising with a visual representation of his or her performance over time for each individual target path. For example, in mode 850, the person exercising is presented with information indicating his or her performance with respect to each of multiple target paths. This information presented to the person exercising enables the person exercising to better identify any particular target paths which the person is having difficulty matching and which improvement may be needed. Such information may also provide the person exercising with an indication as to how fatigue may be affecting the person's performance. For example, such information may indicate that toward the end of workout, the person's correlation score tends to drop. With such information, user may better adjust his or her workout routine such as by adjusting the order or sequence of target paths or adjusting their individual durations per input 30 showing FIG. 9A.

FIG. 9B illustrates a graph which is generated upon display 32 by controller 34 (shown in FIG. 1). In one embodiment, the graph is presented alongside or concurrently with other information such as concurrently with any of the display shown in FIGS. 2-8. In another embodiment, the graph is presented by itself by display 32 in response to a command or other input received from the person exercising.

As shown by FIG. 9B, the graph includes an horizontal axis 852 representing time and a vertical axis 854 representing the correlation score. The time values represented by axis 852 may be universal time values or may comprise elapsed time amounts. The correlation scores provided on axis 854 may have a variety of forms. For example, although axis 854 illustrates scores range from 50 to 100, in other embodiments, axis 854 to alternatively have scores range from zero to 100 or may have other scales or other non-numerical measures of performance.

In the example illustrated, the graph additionally includes a performance line 856. Performance line 56 visually represents the person's correlation score performance over time. In the example illustrated, a performance line is formed from multiple visibly distinct segments 858A, 858B and 858C (collectively referred to as segments 858). Each segment represents the person's performance during a particular target path. In the example illustrated, segment 858A presents a person's performance during the time period which Path A (path 838B shown in FIG. 9A) is the target path. Segment 858A represents a person's performance during the time period which Path B (path 838E shown in FIG. 9A) is the target path. Segment 858C presents a person performance during the time period which Path C (path 838C shown in FIG. 9A) is the target path. When the duration for a particular target path (chosen in FIG. 9A) expires, controller 34 generates control signals initiating the presentation of a new segment representing the next selected target path in the chosen sequence input by the person in FIG. 9A. As the person continues to exercise, new data points, such as flashing pixels or spots, are presented on the display.

In the example illustrated, controller 34 further generates control signals causing display 32 to present a key 860 identifying the Association of segments 858 and paths. In one embodiment, each of segments 858 is represented by distinct graphical symbols along performance line 56. Although segments 858 are illustrated with Xs, Os and check marks, in other embodiments, other graphical symbols may be employed. In yet other embodiments, segment 858 may additionally or alternatively be distinguished from one another by providing segment 858 with distinct colors or line thicknesses. In still other embodiments, segments 858 may be identified or distinguish from one another by labels along performance line 856 or along axis 852, where the labels may include markings indicating the endpoints of such segments.

Although mode 850 is illustrated as utilizing a line graph to provide a person exercising with performance information over time in which one or more target paths are to be matched by the person exercising, in other embodiments, mode 850 may utilize other graphical representations to visually represent the person performance over time. For example, in other embodiments, axis 854 may be omitted, wherein the person's correlation score is represented by a particular color or graphical symbol forming a particular segment 858 along performance line 856. In particular, the different target paths may be represented by different graphical symbols while the colors of the segments may vary depending upon the correlation score. The visual representations of the person's performance over time may have a multitude of different configurations.

Figure 9C:
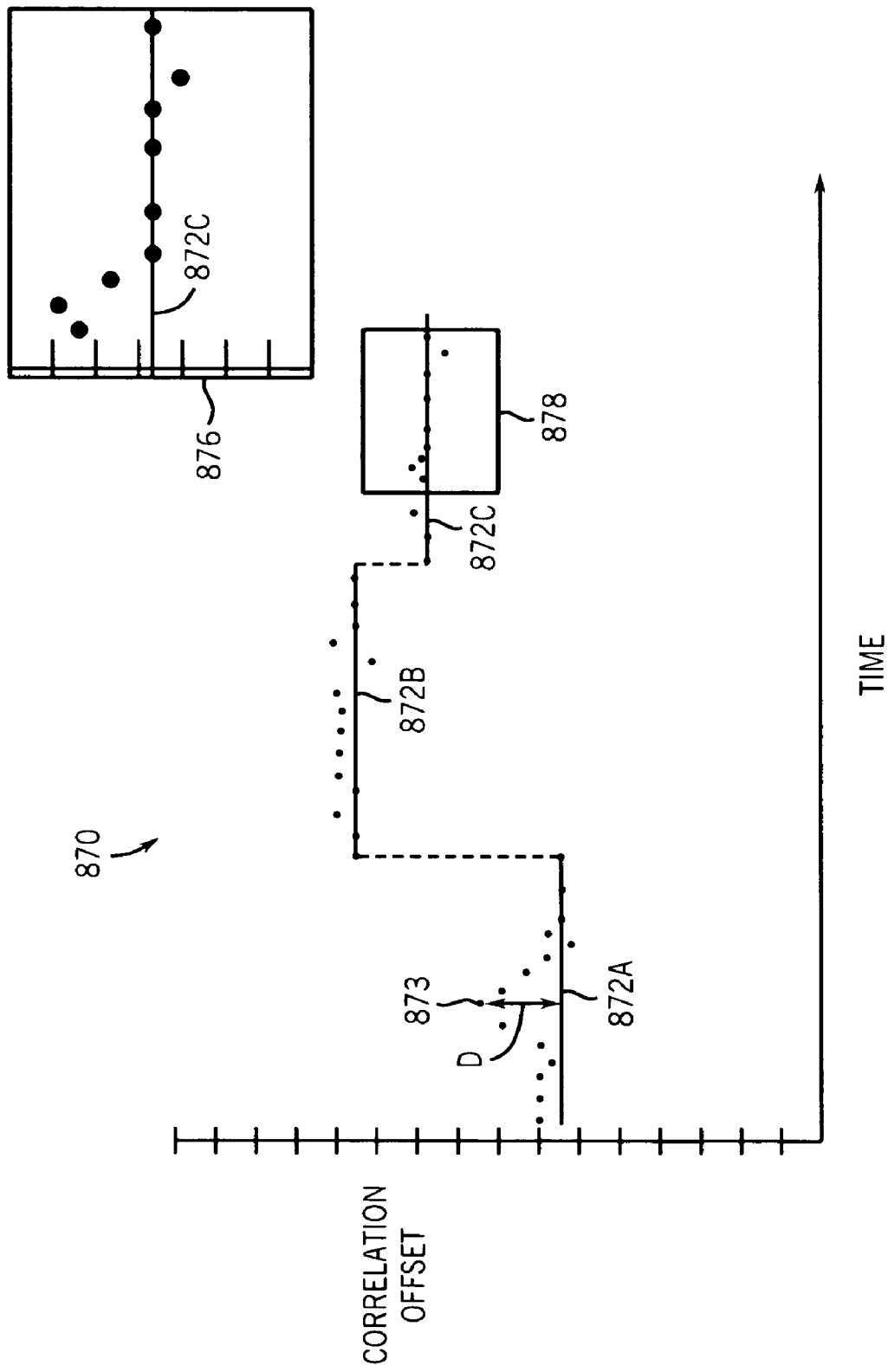
FIG. 9C is a front elevational view of a portion of a screen of an input of the exercise device of FIG. 1 schematically illustrating the display of a correlation offset between target paths and selected paths over time according to an example embodiment.

FIG. 9C illustrates another mode of operation 870 available for exercise device 10 (shown in FIG. 1). In many the previous modes, controller 34 generated control signals causing display 32 to concurrently present the person exercising with a visual representation of the current path taken by the person exercising and the target path. As a result, the person may determine a degree of correlation (correlation offset) between the actual path being taken in the target path from the displayed degree to which the two presented paths matched or overlapped one another at any particular moment in time. In mode 870, controller 34 generates control signals causing display 32 to provide the person exercising with a visual representation of the correlation offset over time. In particular, controller 34 generates control signals causing display 32 to provide visual representations indicating a degree to which the person's actual path(s) matches the selected target path(s) over time.

In contrast to mode 850 which presents a changing correlation score over time, mode 870 provide a visual representation of the extent to which the actual path being taken is offset from or does not match the target path. In particular, motivate 70 presents a graphic representation of the target path and also presents a graphic representation or visual representation of an amount or percentage by which the actual path is offset from the target path. For example, a correlation score of 100 (on a scale of 0-100) would result in mode 870 presenting a data point for the actual path directly on top of or in alignment with the graphical representation of the target path. As the correlation score drops (i.e., the discrepancy increases), the distance separating a particular data point representing the actual path from a corresponding point on the target path increases. For a person exercising, the end objective would be to adapt his or her performance such that the data points representing the actual path being taken move closer to and align with the graphic representation of the target path. Like mode 850, mode 870 enables the person exercising to better evaluate his or her overall workout performance.

In the example illustrated, mode 870 provides graphical representations, lines 872A, 872B and 872C, of target paths 838B, 838E and 838C, respectively (shown in FIG. 9A). Mode 870 further illustrates data points 873 representing the actual path being taken. In one embodiment, data points 873 may be continuously added to the display as a person exercises. In the example illustrated, the offset or discrepancy between the actual path being taken and the target path is visually represented by the distance D separating the data point 873 for the actual path being taken and the line 872 representing the target path. In one embodiment, the distance D depicted on the display screen may correspond to a percentage by which the actual path is offset from the target path. In one embodiment, the percentage may constitute a magnitude such that data point 873 never drops below line 872. In another embodiment, the percentage may be a percentage above or a percentage below the target path, such that the data point 873 may lie above or below line 872. In one embodiment, the distance D may alternatively correspond to or represent a physical quantity by which the actual path differs from the target path. For example, in one embodiment, the distance D on the display screen may represent a vertical distance by which a person's stride (his or her stride height) differs from the target stride height. In another embodiment, the distance D on the display screen may represent a horizontal distance by which a person's stride (his or her stride length) differs from this target stride length. As before, the distance D may merely comprise magnitude or may alternatively additionally indicate whether the stride height or stride length is greater than or less than the target stride height or stride length of the target path.

In the example illustrated, the positioning of the lines 872 along the Y-axis of the graph corresponds to the physical quantity of the target path. For example, in those embodiments in which lines 872 represent a target stride height, line 872 are positioned along the Y-axis of the graph at locations corresponding to the stride heights. In the example illustrated, the target path represented by line 872B has the greatest stride height. Alternatively, lines 872 may represent a target stride length, wherein lines 872 are positioned along the Y-axis of the graph at locations corresponding to the stride length. In the example illustrated, target path represented by line 872A has the shortest stride length. In other embodiments, the different target paths may alternatively visually or graphically represented by a plurality of line segments extending along a single axis.

In one embodiment, controller 34, operating in mode 870, generates additional control signals directing display 32 to present a blowup window 876 (picture in picture) displaying an enlarged portion of the line 872 and data points 873. The portion being enlarged may be graphically represented by a secondary window 878. In the embodiment illustrated, the window 876 additionally includes an enlarged vertical scale corresponding to the Y-axis of the main graph.

In one embodiment, secondary window 78 may be moved in response to commands from the person exercising entered through input 30 (shown in FIG. 1), allowing the person to select those portions of the graph to be enlarged. In another embodiment, secondary window 878 may automatically move so as to present a most recent portion of the exercise routine, for example, the last three minutes of an exercise routine. In one embodiment, mode 870 may permit a person to select the size of window 878 and thereby select the size or amount of time presented in the window 876.overall, window 876 provides an in large scale, allowing a person to better see or evaluate smaller changes in a person's actual path or smaller offsets between the actual path and the target path.

Although the offset is visually represented by the distance or spacing between the line, data points or other graphical representation of the actual path and the line, data points or other graphical representation of the target path in the example illustrated, in other embodiments, the offset may be represented in other manners. For example, in one embodiment, the amount of offset may be represented by a change in color or brightness of the graphical representation of the actual path. In yet another embodiment, the offset that may be represented by changes in the graphical representation or symbols that represent the actual path. For example, for offsets within a first range of percentage points or distances, the actual path may be represented by a first graphical symbol. For offsets within a second range of percent points or distances between the actual path and the target path, the actual path may be represented by a second distinct graphical symbol. In one embodiment, the offset may be represented by both a change in the symbols and a change in colors or brightness of the symbols representing the actual path being taken.

Although mode 870 is illustrated as utilizing a line graph to provide a person exercising with performance information over time in which one or more target paths are to be matched by the person exercising, in other embodiments, mode 870 may utilize other graphical representations to visually represent the person performance over time. For example, in other embodiments, bar graphs or other graphing techniques may be utilized. The visual representations of the person's performance over time may have a multitude of different configurations. Instead of being a mode that a user may toggle or switch to, in some embodiments, mode 870 may be concurrently operated with other modes. For example, the display of mode 870 may be concurrently presented with the other displays described herein.

Figure 10:
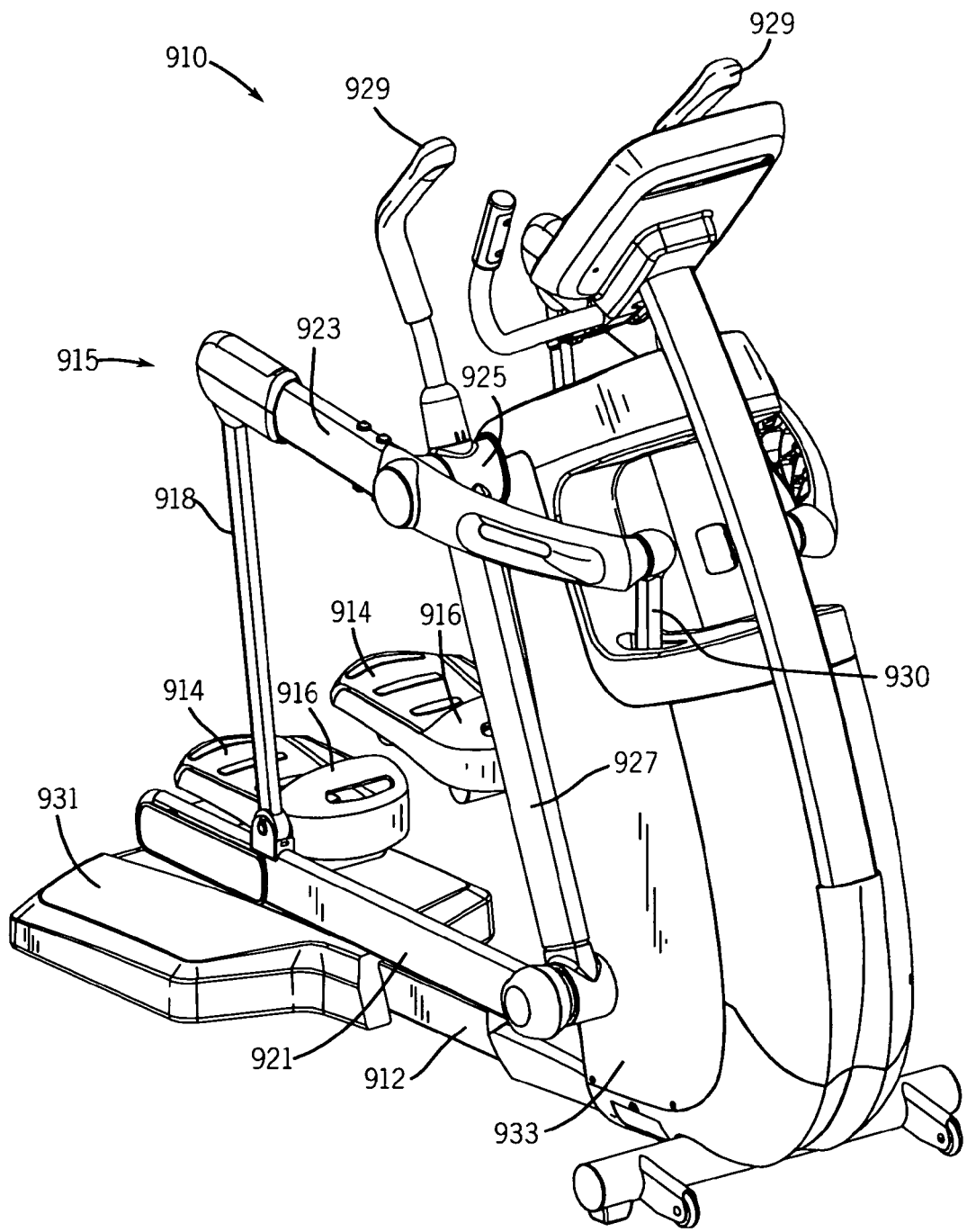
FIG. 10 is a front perspective view of another embodiment of the exercise device of FIG. 1 according to an example embodiment.

FIGS. 10-17 illustrate exercise device 910, a particular embodiment of exercise device 10. In alternative preferred embodiments, other types of exercise machines, including both cardiovascular exercise machines/equipment and weight lifting/strength machines/equipment, providing variable two and/or three dimensional paths of motion for the upper and/or lower body of the user can also be used. Referring to FIG. 10, a perspective view of an embodiment of a pendulum motion-type exercise device 10 is seen. A frame 912 is provided that can include a basic supporting framework. The frame 912 can be any structure that provides support for one or more components of the exercise device 910. A pair of footpads 914 is provided on which the user stands. In one embodiment, a rear support base or platform 931 can be provided connected to the frame 912 that provides further support to the exercise device 910 and acts as a step-up to the footpads 914.

Left and right pivoting linkage pendulum systems 915 are provided. The discussion below will focus on the right pivoting linkage pendulum system 915. However, the description is applicable to the left pivoting linkage pendulum system 15 as well. In one embodiment, the linkage pendulum system 915 includes a lower and upper generally horizontal links 921 and 923, a rear link member 918, a forward generally vertical link 927, and a pivot tube 925 (the pivot tube can be solid or hollow and it serves as a pivot axis). The footpad 914 is coupled to a rear portion of the lower horizontal link 921. The lower horizontal link 21 serves as a foot link linking the footpad 914 to the remaining portions of the pendulum system 915. The lower horizontal link 921 swings or oscillates, but remains generally at or near horizontal, during use. The horizontal link 921 is coupled near its rear end to a lower end of the rear link member 918 and is pivotally coupled at its forward end to the lower end of the forward vertical link 927. The rear link member 918 upwardly extends from its pivotal coupling with the lower horizontal link 921 in a generally vertical direction. The coupling of the rear link member 18 and the lower horizontal link 921 can occur adjacent a forward portion of the footpad 914. The upper end of the rear link member 918 is pivotally coupled to a rear portion of the upper horizontal link 923. The upper horizontal link 923 extends generally horizontally and maintains a position that is generally parallel with the lower horizontal link 921 during use. A central region of the upper horizontal member 923 is pivotally coupled to the pivot tube 925, and a forward end of the upper horizontal member 923 is pivotally coupled to an upper end of a vertical resistance link 930. The pivot tube 925 is directly coupled to the frame 912. The pivotal coupling of the central region of the upper horizontal member 923 to the pivot tube 925 enables the rear portion of the upper horizontal member 923 (a cantilevered end region of the upper horizontal member 923) to be raised upward or downward during use thereby allowing for more pronounced available vertical motion to the exercise device 910 during use. The forward vertical link 927 extends upward, generally vertically, from its coupling at its lower end to the forward end of the lower horizontal link 921. The forward vertical link 927 is pivotally coupled to the upper horizontal link 923 and the frame 912 at the pivot tube 925. Thus, the rear link member 918, the lower and upper horizontal links 921 and 923, the forward vertical link 927, and the pivot tube 925 comprise the pivotal linkage pendulum system 915.

Although the lower and upper horizontal links 921 and 923, and the forward vertical link 927 incorporate the terms horizontal and vertical, these terms are intended to refer to the general orientation of these links. The lower and upper horizontal links 921 and 923, and the forward vertical link 927 will not always lie in a horizontal plane or a vertical plane, respectively. Rather, there positions will remain at or near the respective horizontal or vertical planes during use or while in a rest position.

Additionally, the resistance systems of the present Application are referred to in terms of vertical and horizontal resistance systems. The terms vertical and horizontal, in context of the resistance systems, are used in association with an embodiment of the invention, and the invention is not limited resistances systems that are directed to vertical and horizontal movements only. Rather, the present Application relates to first and second resistance systems, or primary and supplemental resistance systems. The orientation or application of the first and second resistance systems is not limited to vertical and horizontal application only. The present invention involves the application of a second or supplemental resistance system to improve the operation of an exercise device and is not limited to a specific orientation for the second or supplemental resistance application.

A swing arm 929 may be provided by extending the forward vertical link 927 above the pivot tube 925 a predetermined amount. The length and configuration of the swing arm 929 can be varied to match a desired motion and/or feel during use. An aesthetic shroud 933 can partially cover the exercise device 10.

In use, the pivotal linkage pendulum system 915 and the remaining components of the exercise device, enable the user to increase or decrease the stride length or stride of the exercise device as desired. As the user increases his or her stride length or tries to increase his or her cadence, the potential for the foot of the user to disengage, slide or slip from, the footpad 914 increases. Thus, in one embodiment the footpads 914 can be provided with toe clips 916. The toe clips 916 can be fixedly or removably connected to the foot pads 914. In another embodiment, the toe clip 16 and be integrally formed with the foot pad 914. The toe clips 16 enable a user to easily and removably secure his or her foot on the footpad 914 while inhibiting forward movement or forward slippage of the user's foot during use. Accordingly, the toe clips 916 not only properly secure the user's feet with the exercise device 910, but the toe clips 916 also enable the user to readily impart a forward force onto the footpad 914 with the toe clip 916. In some configurations, the toe clips 14 can also enable the user to readily impart an upward force onto the toe clip 916 and foot pad 914 assembly. The user therefore can drive his or her foot forward and even upward without experiencing foot slippage. Additionally, by enabling the user to utilize these additional movements, additional large muscle group involvement is engaged throughout the exercise resulting in higher aerobic training effect. A still further benefit of the use of the toe clips is that more muscles can be exercised throughout the full range of motion rather than just during flexion or just during extension.

Figure 11:
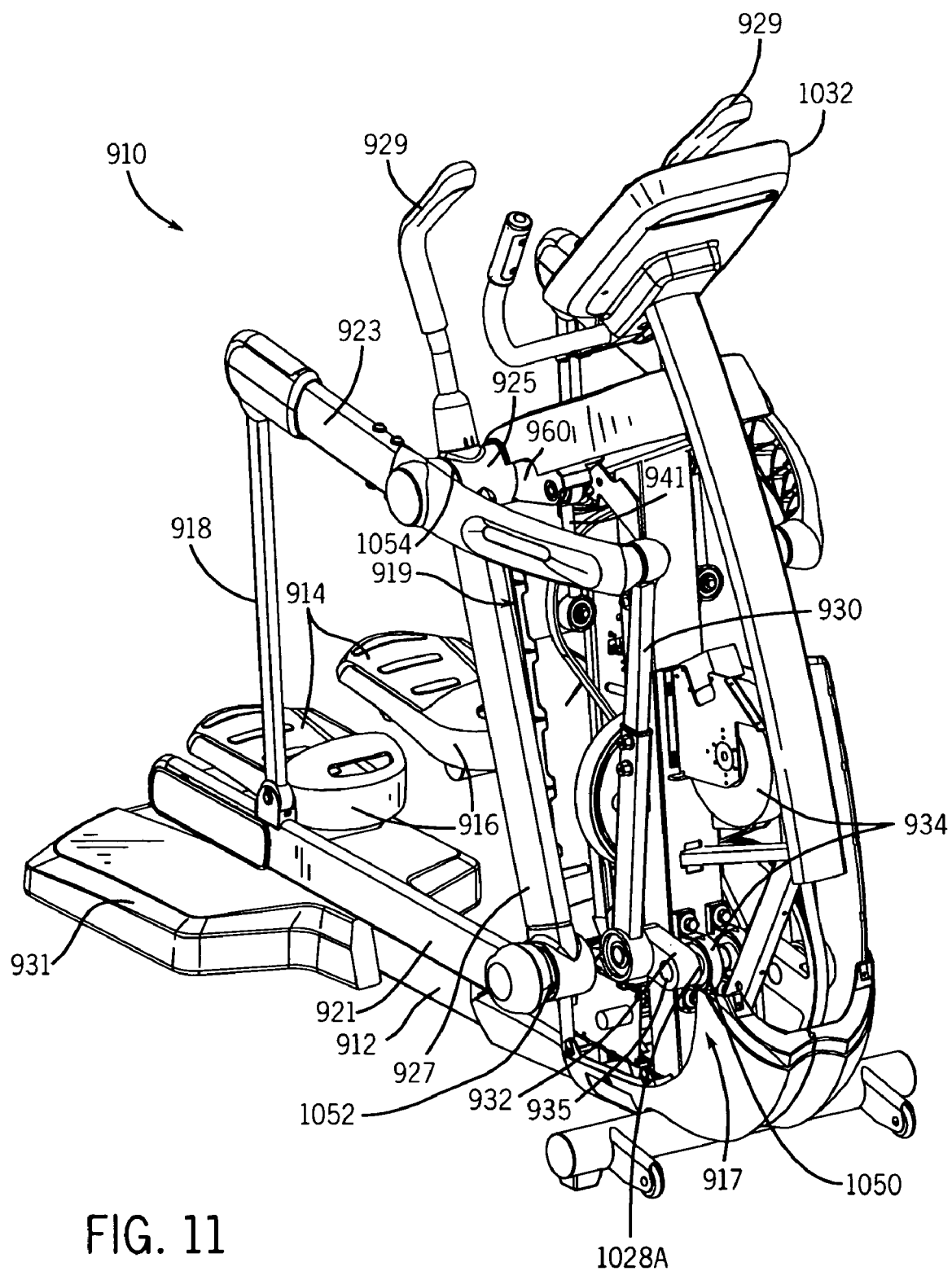
FIG. 11 is a front perspective view of the exercise device of FIG. 10 with a shroud removed according to an example embodiment.

FIG. 11 shows the pendulum motion-type exercise device 910 with the shroud 933 removed. The upper end of the vertical resistance link 930 is pivotally coupled to and extends generally vertically and downward from the forward end of the upper horizontal link 923. At an end opposite the upper horizontal link 923, the vertical resistance link 930 is connected to a generally vertical resistance system 917.

The vertical resistance system 917 can comprise a crank member 932 having a first end that is pivotally coupled to a lower end of the vertical resistance link 930. A second end of the crank member 932 is coupled to a shaft 935. During use, the back and forth motion of the lower horizontal link 921, the rear link member 918, and the forward vertical link 927 typically includes at least some vertical component that causes the upper horizontal link 923 to pivot about its pivotal coupling to the pivot tube 925. This pivotal movement causes the forward end of the upper horizontal link 923 to oscillate upward and downward.

When the user imparts a downward force onto the foot pad 914, or an upward force onto the toe clip 916, these forces also cause the upper horizontal member 923 to pivot or oscillate about its pivotal coupling to the pivot tube 925. This pivotal motion also contributes to the upward and downward oscillating motion of the forward end of the upper horizontal member 923. The shaft 935 and the pivot tube 925 each connect the left and right pivoting linkage pendulum systems 915, and the shaft 935 connects the left and right crank members 932 causes the left and right upper horizontal links 923 to move in opposition to each other (i.e., the right movable member moves downwards as the left movable member moves upwards, and vice versa). The crank member 932 is connected to a pulley system 934, which includes an electronically controlled generator mounted to the frame 912. The pulley system 934 can be preferably operatively connected to a step-up pulley, a flywheel, and a generator system for applying a braking or retarding force, as known in the art. Alternatively, braking or retarding forces can be applied using other mechanisms, such as for example an eddy current system, an alternator, friction brakes, fluid resistance, etc. Thus, a vertical resistance is applied to the upper horizontal link 923 by means of the crank member 932 and the vertical resistance system 917.

The back and forth (fore and aft) path of motion of the exercise device 10 also has a horizontal component. Thus, the exercise device 910 provides for horizontal resistance (a second or supplemental resistance). In particular, the exercise device 910 provides a horizontal resistance system 919 (a second or supplemental resistance system).

Figure 12:
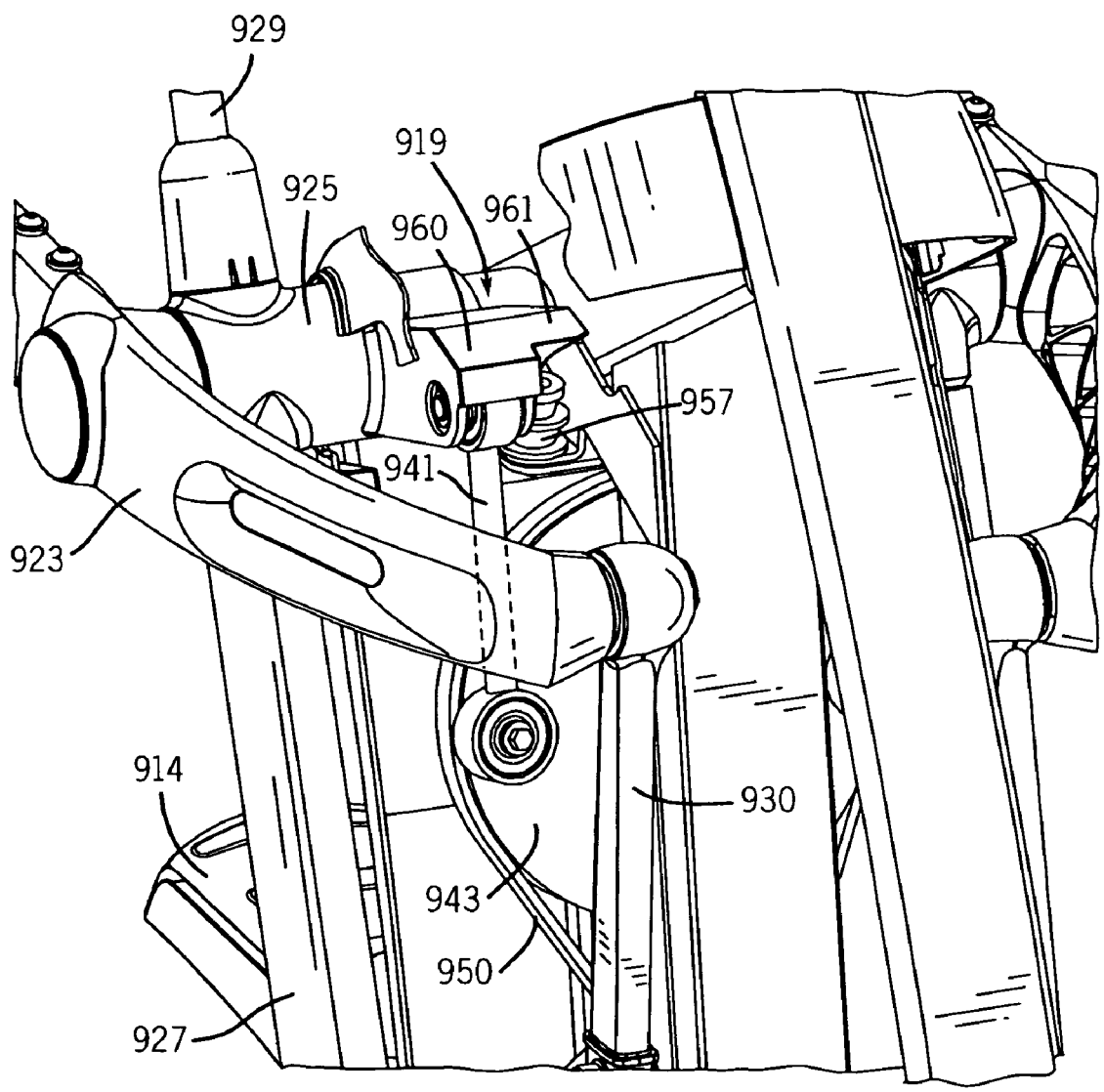
FIG. 12 is a detailed front perspective view of a portion of the exercise device of FIG. 10 according to an example embodiment.

Referring to FIG. 12, a close-up of the pivot tube 925, the upper horizontal link 923, and the vertical resistance link 930 of the exercise device 910 is seen. A supplemental resistance link 41 is provided pivotally coupled to the pivot tube 925 by a rocker link 960 which outwardly extends from the pivot tube 25. The rocker link 960 pivots in coordination with the pivoting movement of the upper horizontal link 923 about the pivot tube 925. At an end of the supplemental resistance link 941 opposite the pivot tube 925, the supplemental resistance link 941 is connected to the horizontal resistance system 919.

The horizontal resistance system 919 can comprise a horizontal resistance pulley 943. The horizontal resistance pulley 943 is pivotally coupled to the supplemental resistance link 941 opposite the pivot tube 925. The supplemental resistance link 941 is pivotally connected to the horizontal resistance pulley 943 near the outer periphery of the horizontal resistance pulley 943; thus the horizontal resistance pulley 943 acts as a crank member pivotally connecting the supplemental resistance link 941 and the horizontal resistance system 919.

Figure 13:
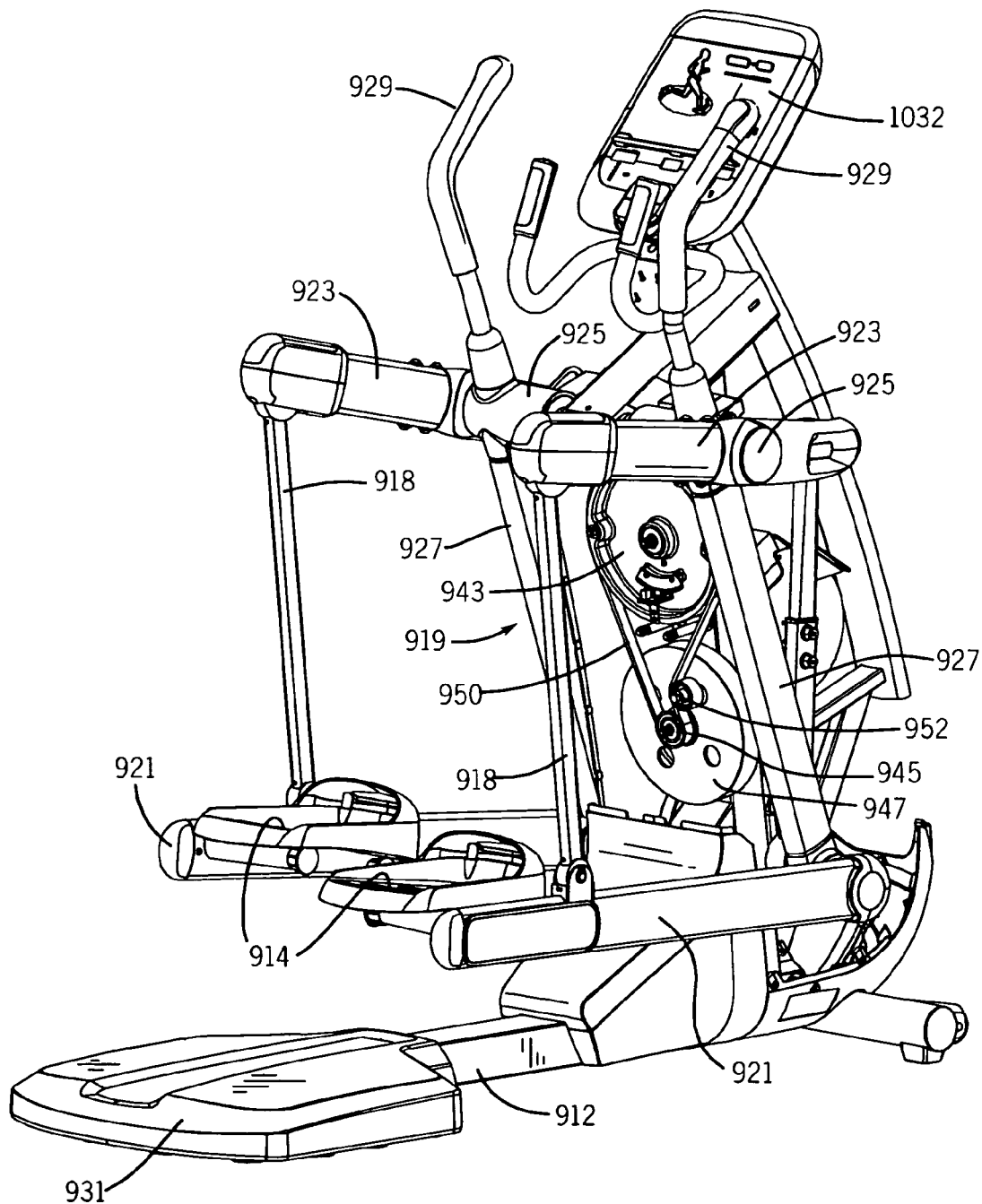
FIG. 13 is a rear perspective view of the exercise device of FIG. 11 according to an example embodiment.
Figure 15:
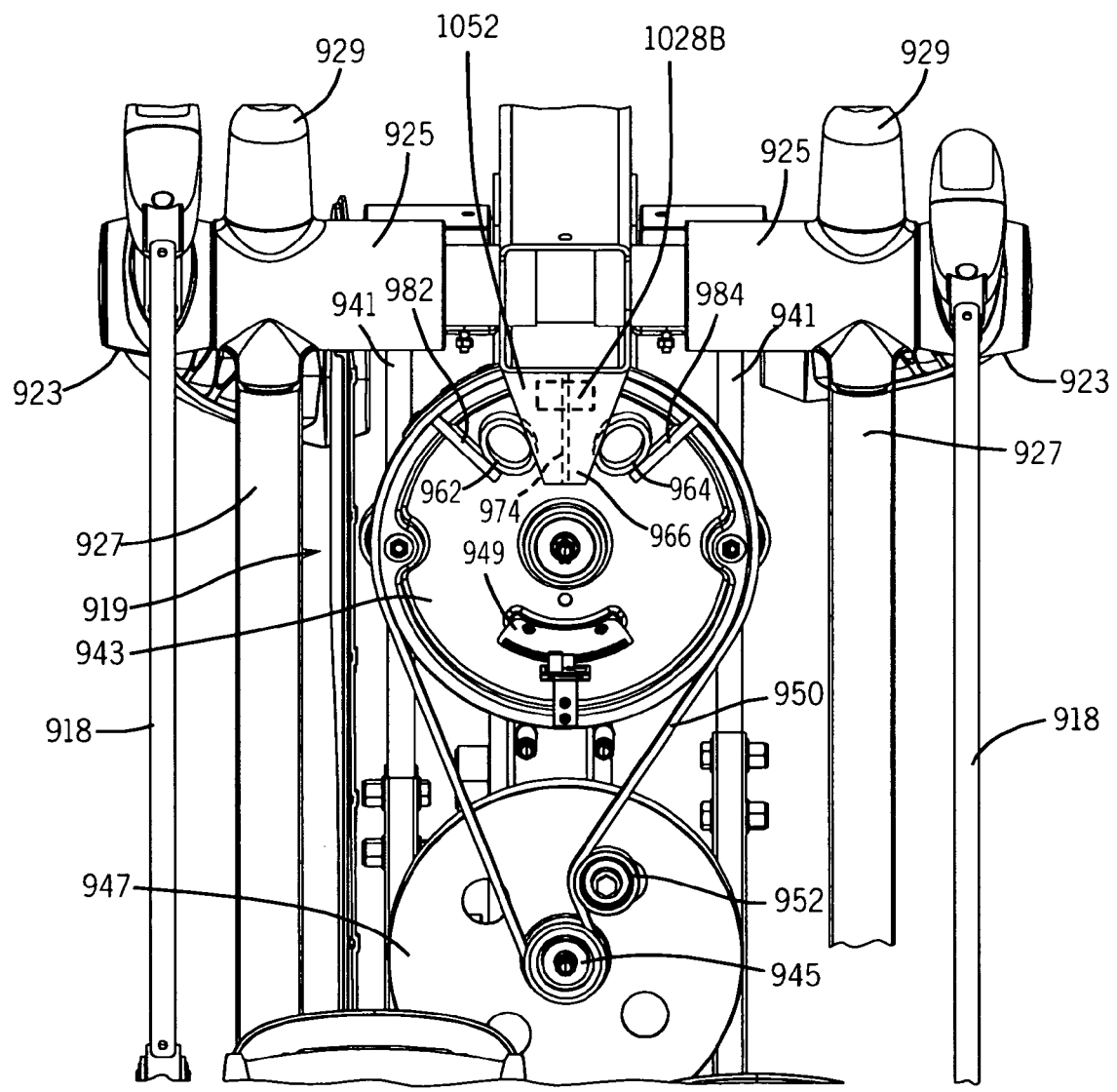
FIG. 15 is a detailed rear elevated view of a portion of the exercise device of FIG. 10 according to an example embodiment.

Referring to FIGS. 13 and 15, the horizontal resistance pulley 943 also acts to provided resistance to the horizontal resistance system. The horizontal resistance pulley 943 is connected to a step-up pulley 945 and a flywheel 947 via a belt 950. Tension on the belt 950 can be maintained via an idler gear 952. In one embodiment, the flywheel 947 can be a rotating metallic flywheel and resistance can be provided by an eddy current brake 949 (seen in FIGS. 15 and 16). The horizontal resistance pulley 943 does not fully rotate in a complete 360 degree revolution; instead, the horizontal resistance pulley 943 rotates through an arch which is determined by the length of the stride of the user. Thus, if the user takes a short stride length, the total rotation of the arch of the horizontal resistance pulley 43 is relatively minimal; if the user takes a long stride length, the total rotation of the arch is relatively significant. By subjecting the rotating horizontal resistance pulley 943 to a means of resistance, the user is subjected to horizontal resistance in the fore and aft motions. In addition, the right and left footpads 914 are synchronized about 180 degrees out of phase by the horizontal resistance pulley 43, the supplemental resistance links 941 and the pivot shaft 925. This synchronization results allow for foot motion that simulates climbing, walking, jogging or running to be achieved. In an alternative embodiment, the right and left footpads 914 can be synchronized by a rocker link or other forms of couplings. In other embodiments, the right and left footpads and the right and left linkage pendulum systems can operate independent of each other or in a non-synchronous manner. In an alternative embodiment, a linear type resistance system can be used in place of the horizontal resistance pulley and related components. The link between the left and right footpads and the left and right linkage pendulum systems can also be accomplished with compliance between the left and right providing a loose or flexible coupling between left and right motions. Also, the movement of the left and right linkage pendulum systems can be configured in a phased operating arrangement.

The horizontal resistance system 919 preferably provides adequate resistance to assist in stable foot motion, but not so much resistance as to make the fore and aft motion unnatural. Excessive resistance in the fore and/or aft directions can cause the foot path to distort in a vertical direction creating an unnatural foot path. In other instances, increased resistance in a fore and/or aft direction can make operation of the exercise device unsustainable for some users. In one embodiment, the level of resistance at the foot pad or the foot of the user in the fore and aft direction is within the range of about 0.5 pounds of force to about 15 pounds of force. The level of resistance can be variable within this range or constant value within this range. The variable resistance can be user adjustable, programmed, time-dependent, or vary based upon other parameters. In another alternative embodiment, the level of resistance at the foot pad or the foot of the user in the fore and aft direction is within the range of about 2.0 pounds of force to about 10.0 pounds of force. The variable resistance can be configured to vary based upon the velocity of the fore and aft motion of the foot pads or the linkage pendulum systems, or the variable resistance can vary based upon user selection, user programs or time or other parameters. The variation in resistance can be obtained by effectively starting and stopping the rotating metallic flywheel 947 of the eddy current brake 949 for fore to aft or aft to fore motions. The metal flywheel 947 is exposed to a magnetic field produced by permanent or electromagnets, generating eddy currents in the wheels. The magnetic interaction between the applied field and the eddy currents acts to slow the metal flywheel 947. The faster the metal flywheel 947 spins, the stronger the effect, meaning the effective horizontal resistance changes for zero force (at zero rotational velocity) to a maximum force at full rotational velocity. A variable resistance can be obtained through linear dampers (magnetic particle shock absorbers), pneumatic or hydraulic shock absorbers, or other non-constant resistance assemblies. Variability of resistance can also be provided by the start and stop of an inertial mass such as a larger flywheel without the need for additional resistance. A constant resistance can be obtained by utilizing a rotating constant torque brake (magnetic particle rotating brake) or other form of friction resistance.

In another embodiment, an electronic controlled horizontal resistance brake can be provided. Use of an electronic controlled horizontal resistance brake allows for pre-determined variations in the resistance throughout the stride, a constant resistance throughout the stride or an overall variability on the effective resistance to assist in interval training. The range of usable resistance at the foot in the fore and aft directions was found to be about 0.5 to about 15 pounds. In another embodiment, a linear resistance system can be provided.

In addition to resistance on the vertical and horizontal movement, the movement of the pivotal linkage pendulum system 915 of the exercise device 910 also includes one or more stops for when the footpad 14 comes to the limit of the exercise device, also referred to as an end of travel stop or an end of travel apparatus. In general, if an end of travel stop is too abrupt, an unsatisfactory jerking will occur to the user; indeed, if this stop is too abrupt and the user is utilizing a fast stride rate, the potential for injury to the user can increase.

Figure 14:
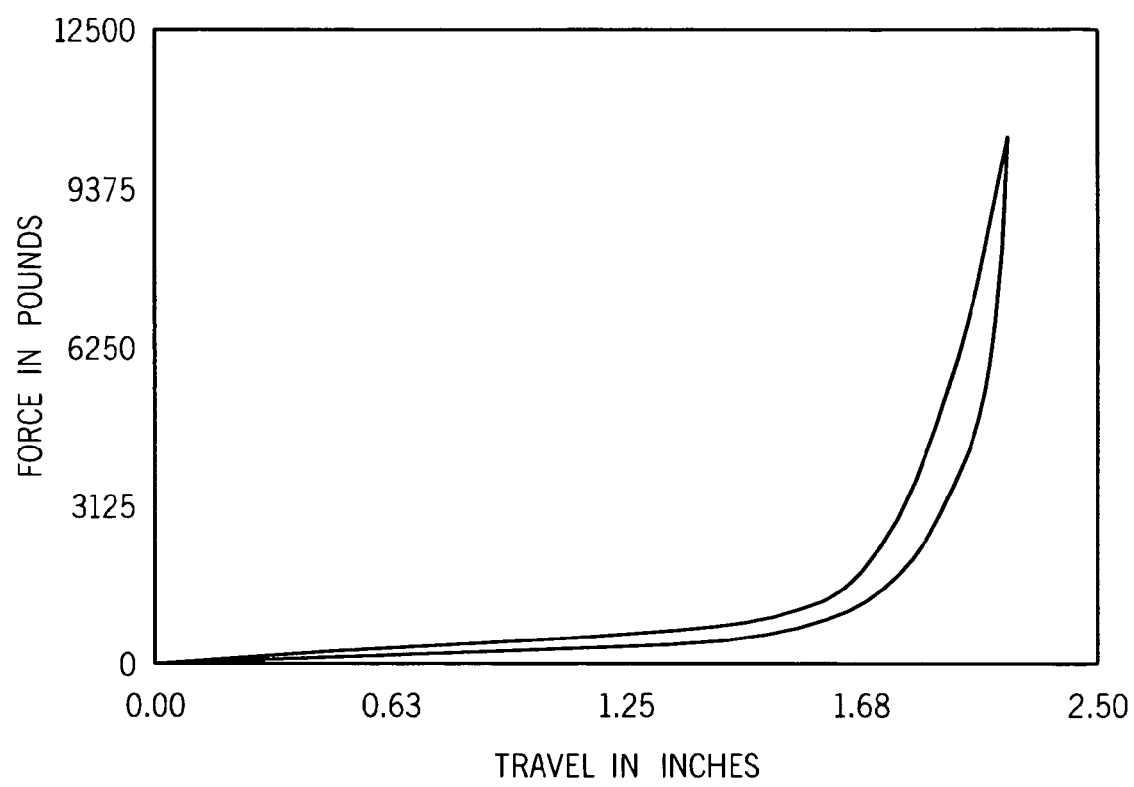
FIG. 14 is a graph of the non-linear profile of the stop point of the exercise device of FIG. 10.

In the example embodiment illustrated, exercise device 910 provides a two-stage linear stiffness profile or a non-linear stiffness profile. This profile is graphed in FIG. 14. In FIG. 14, force in pounds is set forth on the vertical axis and travel in inches is set forth on the vertical axis. It is seen that as the travel increases the force in pounds is initially relatively flat, thereby providing the user with a gentle indication of the end of travel. Then, the force in pounds increases rapidly as the pre-determined stop point is approached. The softer initial contact can also provide a turn-around push for the user, as well as smooth non-forceful signal that the end of travel is approaching.

One embodiment for achieving a two-stage linear or a progressive non-linear stiffness profile is a single bumper that provides a non-linear profile starting off relatively soft at initial contact, then producing an increase in stiffness at a pre-determined stop point. Referring back to FIG. 12, in one embodiment, the rocker link 960 includes stop tab 961 configured to engage a first bumper 957. The first bumper 957 serves as an end of travel stop that provides a highly stiff cushion and a rather abrupt stop when the stop tab 961 fully engages the first bumper 957. As part of the left and right pivoting linkage pendulum systems 915, the exercise device 10 also includes left and right rocker links 961, supplemental resistance links 941 and first bumpers 957.

Figure 16:
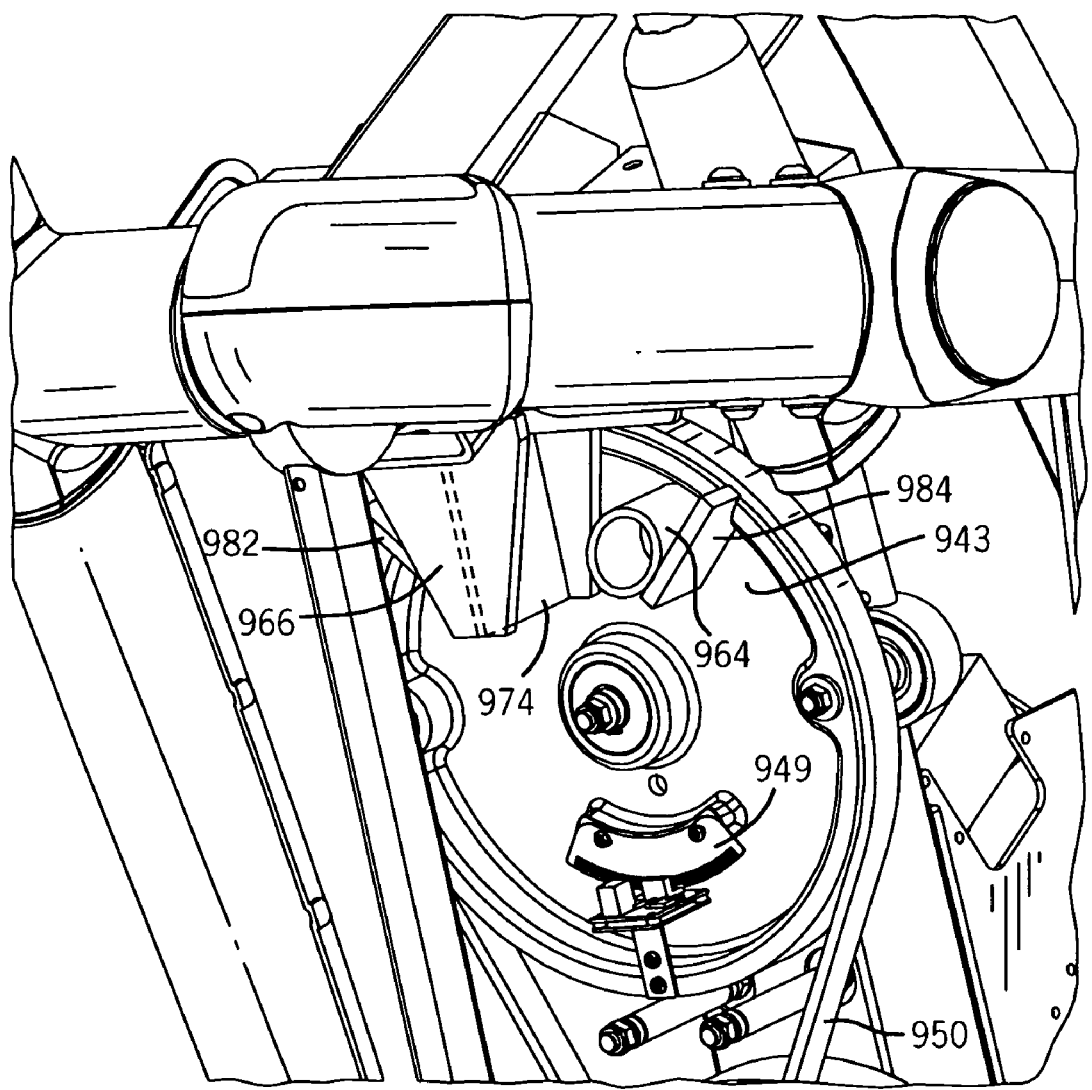
FIG. 16 is a detailed rear perspective view of another portion of the exercise device of FIG. 10 according to an example embodiment.

Referring to FIGS. 15 and 16, in another embodiment, at least a pair of separate second bumpers 962, 964 can be utilized alone, or in combination with the first bumpers 957. In this embodiment, each of the second bumpers 962 and 964 is configured to be relatively soft for the initial contact as the end of travel is approached and then becomes relatively stiff, or increasingly stiff, as the actual end of travel is approached. The first bumper 957, and the second bumpers 962 and 964 are preferably formed of an elastic material such as a polyester elastomer. Alternatively, the first and/or second bumpers can be formed of other materials such as, for example, butyl rubber, polyurethane, other elastomers, or combinations thereof. The elastic properties of the second bumpers 962 and 64 enable the bumpers to provide a gentle push to the user as the user reverses directions at the end of travel position. The gentle push improves the feel and comfort of the exercise device 910 and makes the exercise device more enjoyable to use. In combination, the second bumpers 962 and 964 and the first bumpers 957 provide an optimal two stage end of travel stop configuration for an exercise device in both the fore direction and the aft direction. The second bumpers 962 and 964 provide the initial soft end of travel indication that non-linearly increases if travel continues in the stop direction, and the first bumpers 957 provide the abrupt stop to ensure that the maximum travel of the exercise device is not exceeded, and the exercise device is not damaged, while minimizing the negative impact or feel to the user.

To provide for the at least two second bumpers 962 and 964, in one embodiment, a bumper bracket 966 can be provided extending over the horizontal resistance pulley 943. The bumper bracket 966 contains two contact surfaces 972, 974 adapted to contact and bear against the second bumpers 962 and 964. The second bumpers 962 and 964 are held in brackets 982, 984 contained on the horizontal resistance pulley 943. Thus, as the horizontal resistance pulley 943 comes to the limit of the exercise device 910 as rotating through the arch determined by the length of the stride of the user, one of the second bumpers 962 and 964 held on the horizontal resistance pulley 943 contacts the corresponding contact surface 972 and 974.

The end of travel stop or apparatus is configured to provide a predetermined range of travel after the linkage assembly first contacts the end of travel apparatus. The end of travel apparatus provides first and second ranges of resistance resisting the travel of the linkage assembly over first and second portions of the predetermined range of travel, respectively. One example, of the first and second ranges of resistance is shown on FIG. 14. The first and second ranges of resistance collectively provide a progressive, non-linear stiffness profile to the end of travel apparatus. In one embodiment, the first range of resistance is less than 1000 pounds of force over the first eighty (80) percent of the predetermined range of travel. In one embodiment, the predetermined range of travel of the end of travel stop can be within the range of greater than or equal to one inch to less than or equal to three inches. In another embodiment, the predetermined range of travel of the end of travel stop can be within the range of greater than or equal to 1.5 inches to less than or equal to 2.5 inches. In another embodiment, the first range of resistance is less than 1000 pounds of force over one of the first seventy (70) percent, the first sixty (60) percent or the first fifty (50) percent of the predetermined range of travel.

In another embodiment, the amount of force in pounds applied by the end of travel stop in the second range of resistance is at least 300 percent greater than the amount of force in pounds applied by the end of travel apparatus in the first range of resistance. In other embodiments, the second range of resistance can extends over the last forty percent, the last thirty percent or the last twenty percent of the predetermined range of travel. In other embodiments, the second range of resistance can be at least 400 percent greater, or at least 500 percent greater, than the amount of force in pounds applied by the end of travel apparatus in the first range of resistance.

The end of travel apparatus urges the linkage assembly in a direction opposite the direction at initial contact with the end of travel apparatus after the foot member reaches an initial end of travel position. The second bumpers 962 and 964 are each configured to provide a rebound or a push back in the opposite direction to the horizontal resistance pulley 943, which is ultimately felt by the user during use. This push improves the feel of the exercise device and further reduces any negative feedback resulting from engaging the end of travel stop or apparatus. The end of travel apparatus or assembly preferably provides a coefficient of restitution ("COR") of at least 0.60 percent. COR is a measure of energy loss or retention, and refers to the ratio of outgoing energy (also displayed in terms of speed or force) to incoming energy (also speed or force) of the linkage assembly engaging the end of travel apparatus or assembly. In another embodiment, the end of travel apparatus or assembly produces a COR of at least 0.70.

Overall, exercise device 910 provides a user with a variety of smooth natural available exercise paths or foot motions, exercises a relatively large number of muscles through a large range of motion, and provides such foot motions in a safe and stable manner. Exercise device 910 also provides an exercise device having available resistance in more than one general direction, such as resisted free travel in the fore and aft directions, without detracting from the engaging motion of the exercise device.

As discussed above with respect to exercise device 10, the relatively large freedom of motion or number of available paths provides for a more dynamic and potentially less monotonous work out. At the same time, the freedom of motion provided by exercise device 10 may make it more difficult for a user to maintain proper form for a desired particular path or to evaluate progress towards a fitness goal. To address such issues, exercise device 910 edition includes feedback system 1012.

Feedback system 1012 provides a user who is exercising with visual feedback regarding the actual taken path. Feedback system 1012 further provides a user with the ability to visually compare his or her actual taken path with one or more target paths. Feedback system 1012 includes sensors 1028A and 1028B (collectively referred to as sensors 1028), and console 1029 which includes input 1030, display 1032 and controller 1034 (schematically represented).

Sensors 1028 sense or detect the actual path being taken and the current position of foot rest 914 along the actual path. Signals representing detect the actual path being taken and the current position of foot rest 914 along the actual path are transmitted to controller 1034 which uses such information to generate control signals causing display 1032 provided or representations of the actual path being taken and one or more target paths. In particular embodiment, controller 1034 may also use such information to generate a score indicating a degree of matching or correlation between actual path and the desired target path.

As shown by FIG. 11, in the example illustrated, sensor 1028A comprises an angle sensor, such as an optical encoder including, not limited to, a quadrature encoder. located between crank member 932 and a stationary structure or frame portion 1050 opposite to crank member 932. Sensor 1028A detects the vertical positioning of the associated foot rest 14.

In other embodiments, sensor 1028A may be located at other positions and may comprise other type as sensors. For example, sensor 1028A to alternatively be located at locations 1052 or 1054. In other embodiments, sensor 1028A may alternatively comprise other type as sensors such as a Hall effect sensor, a magnetoresistive sensor, a magnetic potentiometer or the like.

As shown in FIG. 15, sensor 1028B comprise a sensor configured to sense a stride length (reciprocal back and forward motion of foot rest 14). In the example illustrated, sensor 1020 comprises an angular sensor such as an optical encoder (quadrature encoder) located between horizontal resistance pulley 43 and a stationary structure or frame 1052. Sensor 1028B detects angular rotation of pulley 43 which corresponds to the generally horizontal positioning of foot rests 14.

In other embodiments, sensor 1028b may be located at other positions and may comprise other type as sensors. For example, sensor 1028A to alternatively comprise other type as sensors such as a Hall effect sensor, a magnetoresistive sensor, a magnetic potentiometer or the like.

Console 1029 is supported by frame 912 and includes input 1030, display 1032 and controller 1034. Input 1030 comprises one or mechanisms configured to permit the entry of selections, commands and/or data into exercise device 910. In one embodiment, input 1030 may be configured to facilitate entry of such selections, commands or data by the user of exercise device 910. In the example illustrated, input 1030 comprises a series of buttons which may be depressed. In other embodiments, input 1030 may alternatively comprise a touchpad, a touch screen, a keyboard, a mouse, or more dials, one or more rocker switches or a microphone and appropriate voice transcription or recognition software.

In the example illustrated, input 1030 additionally includes devices facilitating reception of data or instructions from external electronic sources. In the example illustrated, input 1030 includes an electronic plug-in or port 1038, wireless communication interface 1040 and memory card slots 1042. Port 1038 comprises a plug-in by which external electronic devices may be releasably wired or removably connected to console 1029. One example such a port is a USB port.

Wireless communication interface 1040 comprises an interface configured to receive and transmit wireless signals via a wireless network, infrared waves or other wireless communication formats. Memory card slot 1042 comprises a slot configured to receive and connect a memory card reader/writer to a portable memory card. Memory card slot 1042 enables exercise device 910 to receive exercise routines (containing sequences of target path) from a memory card. In other embodiments, console 1029 may include other devices facilitating such communication. In yet other embodiments, one or more of plug-in 1038, wireless medication interface 1040 and/or memory card slot 1042 may be omitted.

Display 32 comprises a monitor, screen or other device configured to present visual information to a user of exercise device 10 while the user is exercising. In the example illustrated, display 1032 comprises a LCD screen. In another embodiment, display 32 may comprise an array or series of individual lights or light emitting diodes that are selectively eliminated provide visual information. In one embodiment, display 1032 may be a part of a touch screen which also serves as input 1030.

As shown my FIG. 13, display 1032 is fixedly mounted to frame 912 and supported such that a person may view display 1032 when exercising. In yet another embodiment, display 1032 may be provided by a portable device which is removably connectable to exercise device 910. For example, display 32 may be provided by a handheld personal data device such as a personal digital assistance (PDA), portable media player (such as an IPOD), MP3 player or similar portable device having a display which is connected to controller 1034 via a plug-in or port or wirelessly, wherein the portable device is supported by frame 912 during such exercise or is held by the user exercising.

Controller 1034 (schematically shown) comprises one or more processing units configured to receive signals from sensors 1028, to receive selections, commands or data from input 1030 and to generate control signals directing the operation of at least display 1032 and potentially additionally directing vertical resistance system 17 and horizontal resistance system 19 which serve as resistance supplies. In the embodiment illustrated, controller 1034 generates control signals based upon signals received from sensors 1028 that cause display 1032 to present a visual representation of the path taken by at least one of foot rests 914. Controller 1030 for further generates control signals based upon a desired target path to cause display 1032 to concurrently present a visual representation of the target path with the presentation of the actual path.

In the example illustrated, controller 1 034 generates control signal such that the actual path 1136 is overlaid with respect to the target path 1138. The actual path 1136 ("YOUR PATH") is represented by a series of five illuminated circles or dots for each leg. The dots represent the portion of the path currently being traversed. As the person moves along the actual path being taken, the dots also move on the screen in the shape of the path being taken. In other embodiments, the actual path 1036 may be visually represented in other fashions.

The target path 1138 is represented by a distinct series of graphical symbols. In the example illustrated, target path 1138 is represented by a series of short linear marks or dashes. The shape of the series of the dashes changes based upon the particular desired target path for the particular moment in time. In other embodiments, the target path may be visually represented in other fashions.

Feedback system 1012 enables a person exercising to visually see his or her actual path and to visually compare it with a target path. As a result, the person exercising may be better able to make adjustments to meet the target path. In the example illustrated, each of the five dots representing positioning of the persons two feet along the actual path 1136 is just inside of the target path 1138. This generally means that the actual path being taken by the person, his or her stride, needs to be longer as well is vertically elongated. As the person attempt to make such changes, he or she will notice that the positioning of the circles representing the actual path 1136 also move. The person exercising can visually align the resulting docs or circles forming actual path 136 with the target path 1138 to achieve the target path 1138.

Figure 17:
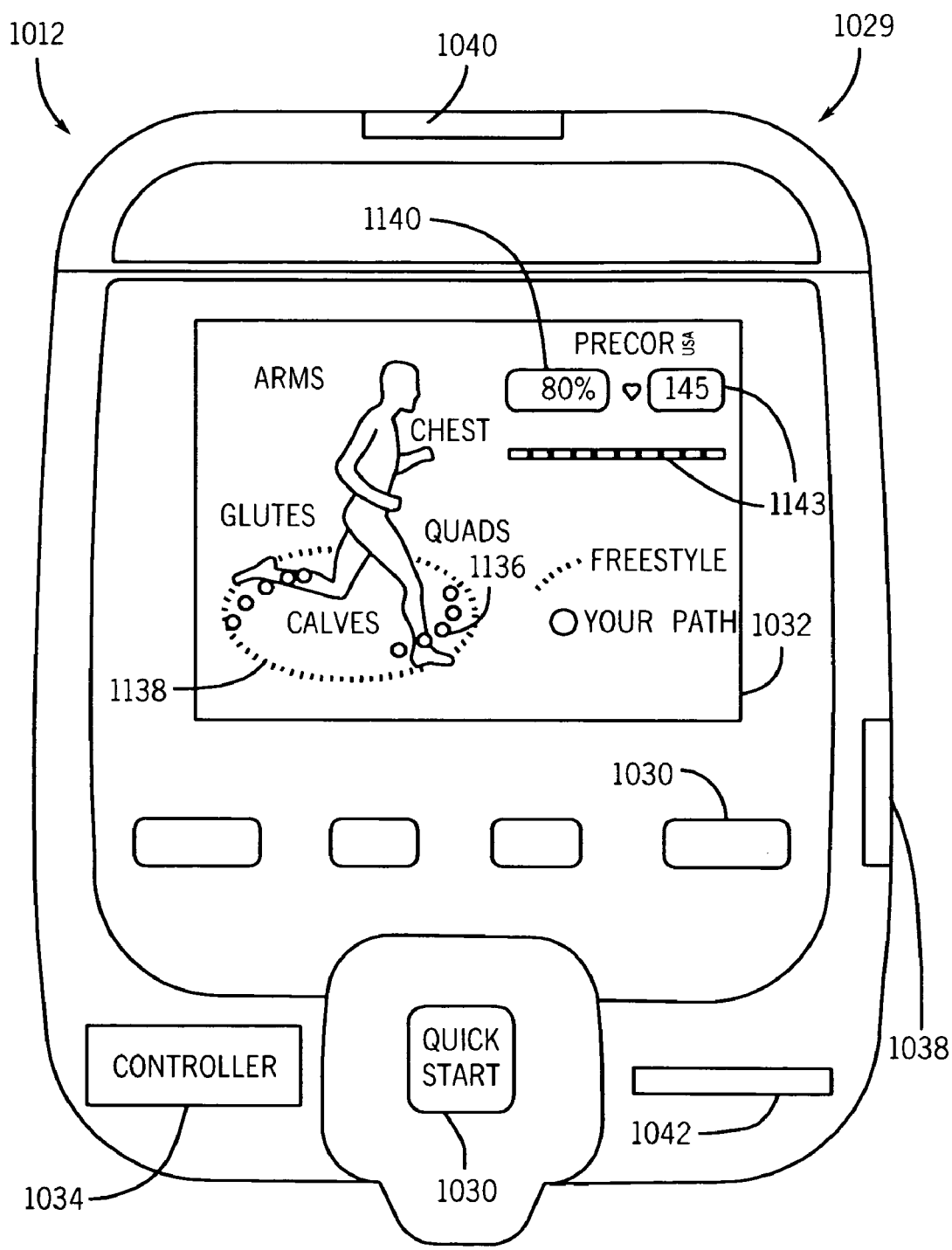
FIG. 17 is front elevational view of a console of the exercise device of FIG. 10 having a display presenting visual representations of an actual path and a target path according to an example embodiment.

As shown in FIG. 17, display 1032 further presents other metrics. For example, display 1032 additionally presents a score 1140 indicating a degree of matching or correlation between the actual path 1136 and the target path 1138. Display 1032 also presents metrics 1143 corresponding to the person's detected heart rate. In other embodiments, various other metrics may also be displayed such as the total calories burned during an exercise routine or the rate at which calories are being burnt during a particular exercise routine.

The depicted display 1032 is but one example of one mode under which feedback system 1012 may operate. In particular, feedback system 1012 may be configured to operate in multiple modes which may be selected by a user using input 1030. For example, feedback system 1012 may be configured to operate in any of the modes shown and described above with respect to FIGS. 2-7. Feedback system 1012 may operate in multiple molds at any one time. Likewise, feedback system 1012 may provide motivational graphics such as shown and described with respect to FIG. 8 and may facilitate programming or entry of an exercise routine such as shown and described with respect to FIG. 9.

Feedback system 1012 may also receive exercise routines from external sources. For example, in one embodiment, exercise routines may be received via port 1038, wireless communication interface 1040 or memory card slot 1042. Such exercise routines may be downloaded from a network or Internet or maybe contained on portable disks, cards or the like. Such exercise routines may be supplied by the user's trainer, the exercise routines customized for the particular users exercise objectives.

In one embodiment, a trainer may go through an exercise routine, wherein the trainer's exercise routine (the sequence of paths taken by the trainer on a similar exercise device) are sensed or otherwise captured by camera or one or more sense as associate with the trainer to exercise device similar or identical to the exercise device being used by the user. The sensed or captured exercise routine is analyzed and broken down into the one or more paths actually taken by the trainer. This analysis of the actual paths taken by the trainer and conversion to target paths for use by the trainees may be performed by controller 34 or by a controller or one or more processing units external to the exercise device of the user, such as an external computer or server. These actual paths taken by the trainer are then either stored for subsequent use as target paths by one or more users or are transmitted in real time (substantially instantaneously as the trainer is going through the desired routine for the trainees) via a network or intranet as target paths to multiple users or trainees.

The above method enables multiple users, potentially at remote locations, to follow the actions of a trainer, simulating an exercise class provided by the trainer. At the same time, in addition to observing the trainer on his or her monitor screen or in person, the person exercising may also observe a visual representation of the actual movements or paths taken by the trainer on his or her display 1032. On top of this, the user who is exercising also receives a score or indication of how well he or she is mimicking or following the trainer during an exercise routine. The score would indicate the degree of correlation between the actual paths or motions taken by the user who is exercising to the actual paths or motions taken by the trainer which are used as the "target" paths.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted the claims reciting a single particular element also encompass a plurality of such particular elements.

What is claimed is:

1. An exercise device comprising:
   a frame;
   a first member movably coupled to the frame and configured to move through a first selected one of a first plurality of different available paths and to change between the first plurality of different available paths in response to force applied by a person to the first member;
   a display; and
   a controller configured to generate control signals causing the display to present a first visual representation of the first selected one of the first plurality of different available paths comprising a current path being taken by the first member, wherein the controller is further configured to generate control signals causing the display to present a second visual representation of a second one of the first plurality of different available paths which is different than the first visual representation and which comprises a target path and wherein the first visual representation and a second visual representation are concurrently presented by the display.

2. The exercise device of claim 1 further comprising:
   a second member movably coupled to the frame and configured to move through a second selected one of a second plurality of different available paths.

3. The exercise device of claim 2, wherein the controller is further configured to generate control signals causing the display to present a second visual representation of the second selected one of the second plurality of different available paths.

4. The exercise device of claim 2, wherein the first plurality of different available paths and a second plurality of different available paths are identical.

5. The exercise device of claim 2, wherein the first plurality of different available paths and the second plurality of different available paths are ovular and wherein movement of the second member along the second selected one of the second plurality of different available paths is substantially 180 degrees out of phase with respect to movement of the first member along the first selected one of the first plurality of different available paths.

6. The exercise device of claim 2, further comprising a resistance supply configured to supply a user selectable level of resistance against movement of the first member and the second member.

7. The exercise device of claim 2, wherein the first member and the second member are configured to be controlled by a user's feet and to be moved in response to movement of the user's legs.

8. The exercise device of claim 2 further comprising a third member configured to be grasped by a user's first hand and coupled to the first member so as to substantially move with the movement of the first member.

9. The exercise device of claim 1 further comprising a resistance supply configured to supply a user selectable level of resistance against movement of the first member.

10. The exercise device of claim 1, wherein the first member includes a platform configured to extend below and elevate a user's foot.

11. The exercise device of claim 1, wherein the first plurality of different available paths are selected from a group of path shapes consisting of: elliptical, circular, reciprocal and 3-dimensional.

12. The exercise device of claim 1, wherein the first plurality of different available paths includes a first path and a second path extending in x and y orthogonal axes in space, wherein the first path includes a first point having a first y-axis coordinate and a first x-axis coordinate and wherein the second path includes a second point having a second y-axis coordinate and the first x-axis coordinate.

13. The exercise device of claim 1, wherein the first plurality of different available paths includes paths having different vertical extents.

14. The exercise device of claim 13, wherein the first plurality of different available paths includes paths having different horizontal extents.

15. The exercise device of claim 1, wherein the controller is configured to generate control signals causing the display to present a motivational graphic that changes based upon correlation between the first selected one of the first plurality of available different paths and a second one of the first plurality of available different paths different than the first selected one of the plurality of different available paths.

16. The exercise device of claim 1, wherein the controller is configured to generate control signal such that the motivational graphic and a first visual representation are concurrently presented by the display.

17. The exercise device of claim 16, wherein the controller is configured to generate control signals such that the second visual representation, the first visual representation and the motivational graphic are concurrently presented by the display.

18. The exercise device of claim 1, wherein the controller is configured to generate control signals causing the display to present a numerical or letter score based upon correlation between the first selected one of the first plurality of different available paths and a second one of the first plurality of different available paths different than the first selected one of the first plurality of different available paths.

19. The exercise device of claim 1, wherein the first visual representation is a visual animation of an anatomy of a user moving along the first selected one of the first plurality of available different paths.

20. The exercise device of claim 1, wherein the first visual representation comprises a visual representation of an entirety of the first selected one of plurality of different available paths.

21. The exercise device of claim 20, wherein the first selected one of the first plurality different available paths comprises a non-circular loop and wherein the first visual representation further comprises an indication of a current location of the first member along the first selected one of the plurality of different available paths.

22. The exercise device of claim 1, wherein the first selected one of the first plurality of different available paths comprises a non-circular loop and wherein the first visual representation comprises an indication of a current location of the first member along the first selected one of the plurality of different available paths.

23. The exercise device of claim 1, wherein the first visual representation comprises a segment of and not an entirety of the first selected one of plurality of different available paths, wherein the segment encompasses a current location of the first member along the first selected one of the plurality of different available paths.

24. The exercise device of claim 1 wherein the controller is configured to generate control signals causing the display to vary at least one non-shape characteristic of first visual representation based upon correlation between the first selected one of the first plurality of different available paths and a second one of the first plurality of different available paths different than the first selected one of the first plurality of different available paths.

25. The exercise device of claim 1 further comprising an input configured to permit a user to identify one of the first plurality of different available paths as a target, wherein the first selected one of the first plurality of different available paths comprises a non-circular loop and wherein the controller is configured to compare the first selected one of the first plurality of different available paths to the target.

26. The exercise device of claim 1 further comprising an input configured to permit a user to identify a sequence of different paths from the first plurality of different available paths as a target, wherein the controller is configured to compare actual movement of the first member to the target.

27. The exercise device of claim 1, wherein one of the first plurality of different available paths has a vertical amplitude and a horizontal amplitude and wherein the vertical amplitude is greater than or equal to the horizontal amplitude.

28. The exercise device of claim 1, wherein the controller is configured to generate control signals causing the display to present a visual representation concurrently representing a plurality of correlation offsets between target paths and corresponding selected paths at different times over time.

29. The exercise device of claim 1, wherein the controller is configured to generate control signals causing the display to present a visual representation of a correlation score between target paths and corresponding selected paths over time.

* * * * *